United States Patent
Kriesel et al.

[11] Patent Number: 5,957,891
[45] Date of Patent: Sep. 28, 1999

[54] FLUID DELIVERY DEVICE WITH FILL ADAPTER

[75] Inventors: Marshall S Kriesel, St. Paul; Farhad Kazemzadeh, Bloomington; Matthew B. Kriesel, St. Paul; Steven C. Barber, Shorewood, all of Minn.; William J. Kluck, Hudson, Wis.; William W. Feng, Lafayette, Calif.

[73] Assignee: Science Incorporated, Bloomington, Minn.

[21] Appl. No.: 08/991,123

[22] Filed: Dec. 16, 1997

Related U.S. Application Data

[63] Continuation-in-part of application No. 08/606,090, Feb. 23, 1996, Pat. No. 5,779,676, which is a continuation-in-part of application No. 08/541,184, Oct. 11, 1995, Pat. No. 5,776,103.

[51] Int. Cl.$^6$ .................................................. A61M 37/00
[52] U.S. Cl. ...................... 604/132; 604/890.1; 604/246; 128/DIG. 12
[58] Field of Search .................................... 604/131, 132, 604/151, 153, 890.1, 246; 128/DIG. 12

[56] References Cited

U.S. PATENT DOCUMENTS

| | | | |
|---|---|---|---|
| 4,193,397 | 3/1980 | Tucker et al. | 604/83 |
| 4,258,711 | 3/1981 | Tucker et al. | . |
| 4,511,355 | 4/1985 | Franetzki et al. | 604/131 |
| 4,539,004 | 9/1985 | Eckenhoff et al. | 604/131 |
| 4,668,231 | 5/1987 | DeVries | 604/891 |
| 4,838,887 | 6/1989 | Idriss | 604/891.1 |
| 4,968,301 | 11/1990 | Di Palma | 604/132 |
| 4,969,873 | 11/1990 | Steinbach et al. | 604/93 |
| 5,019,047 | 5/1991 | Kriesel | 604/132 |
| 5,330,426 | 7/1994 | Kriesel et al. | 604/89 |
| 5,848,991 | 12/1998 | Gross et al. | 604/140 |

*Primary Examiner*—Corrine McDermott
*Attorney, Agent, or Firm*—J.E. Brunton

[57] ABSTRACT

A fluid delivery device having a self-contained stored energy membrane for expelling fluids at a precisely controlled rate which is of a compact, laminate construction. The device also includes a novel adapter which is usable to fill the reservoir of the device using a compatable filling syringe apparatus which is mateable with the adapter.

29 Claims, 16 Drawing Sheets

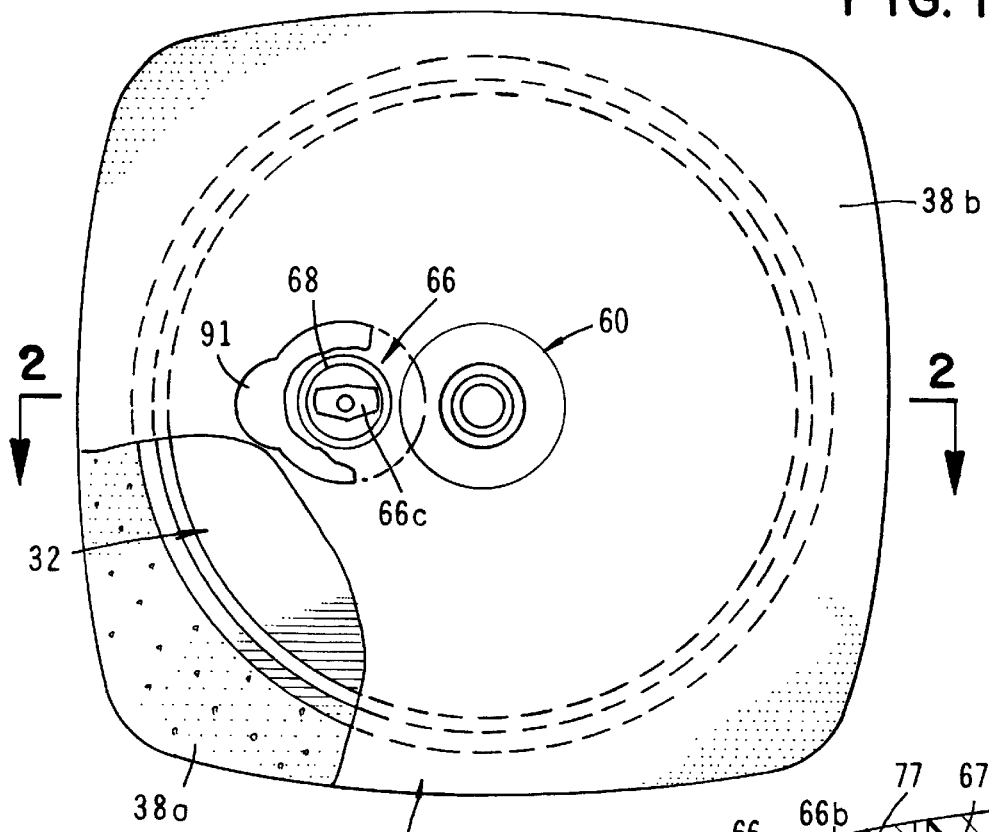
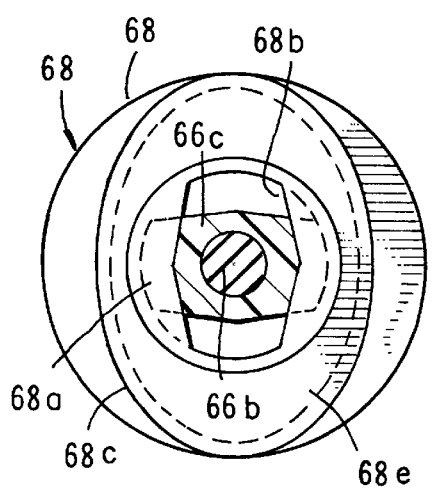
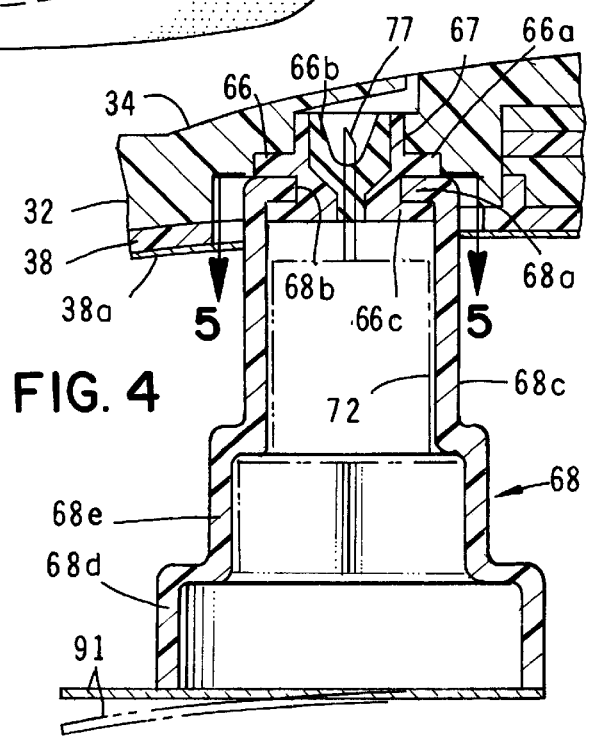
FIG. 1
FIG. 4
FIG. 5

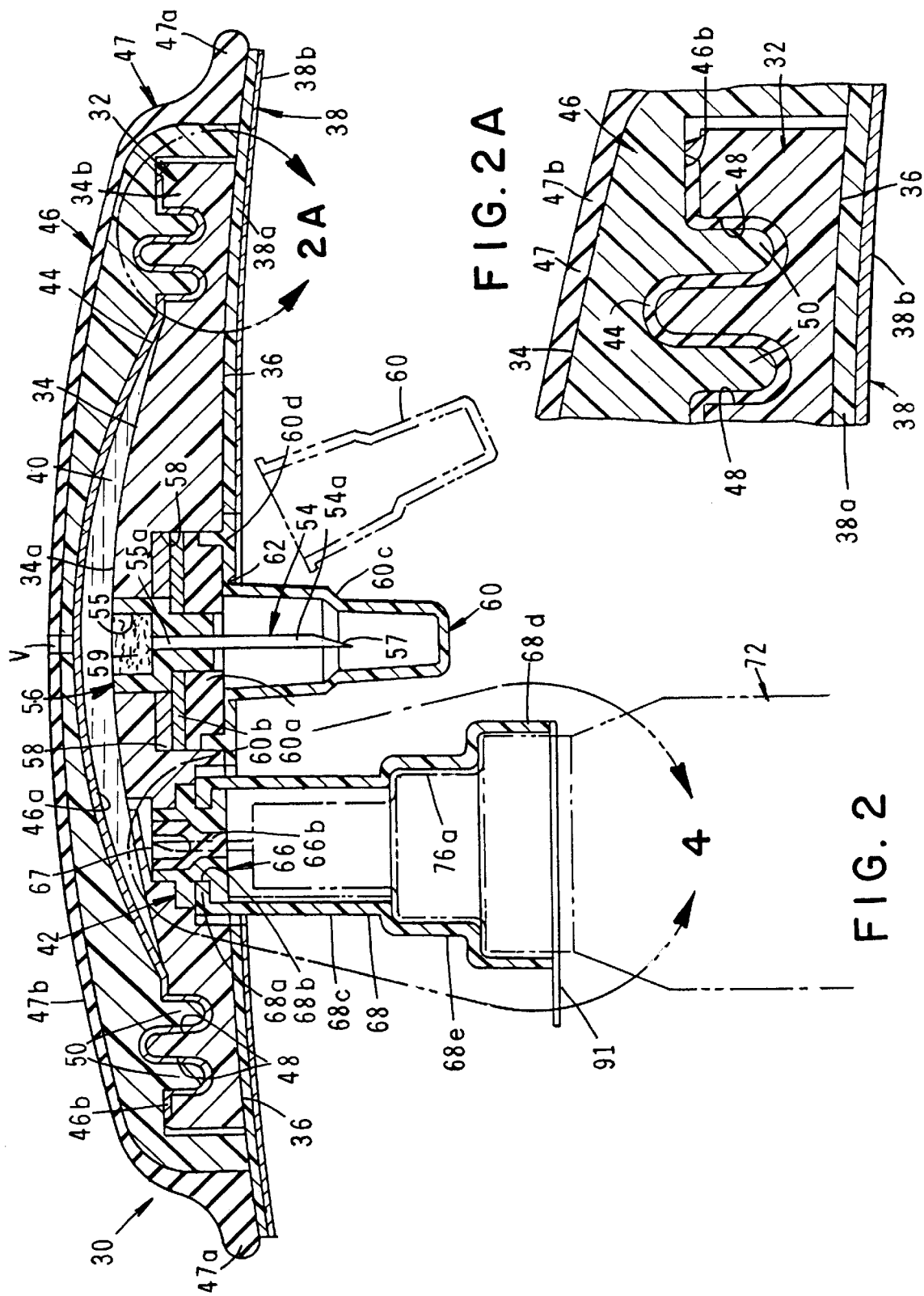

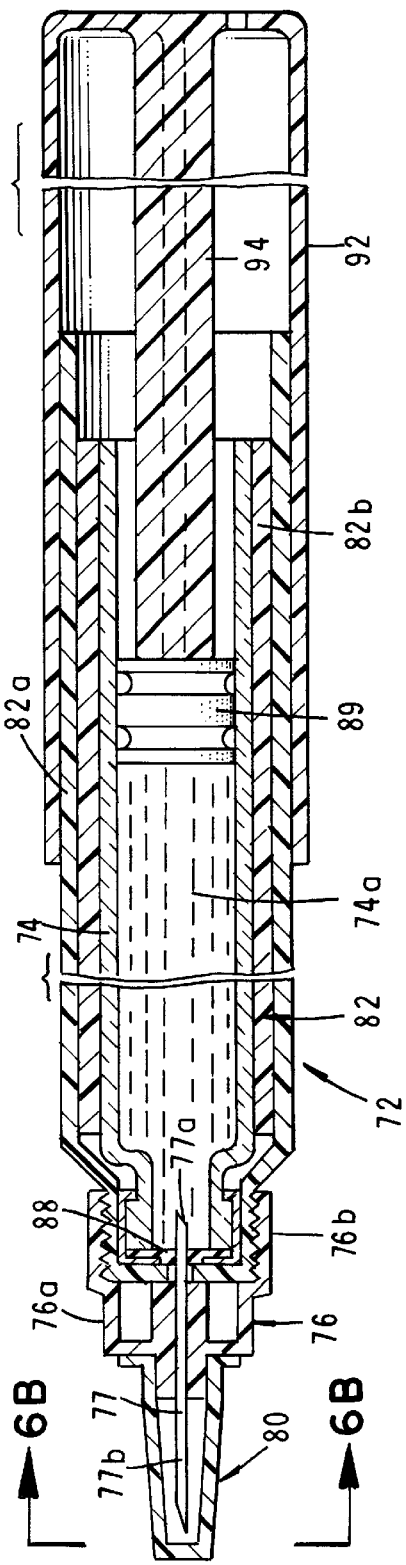
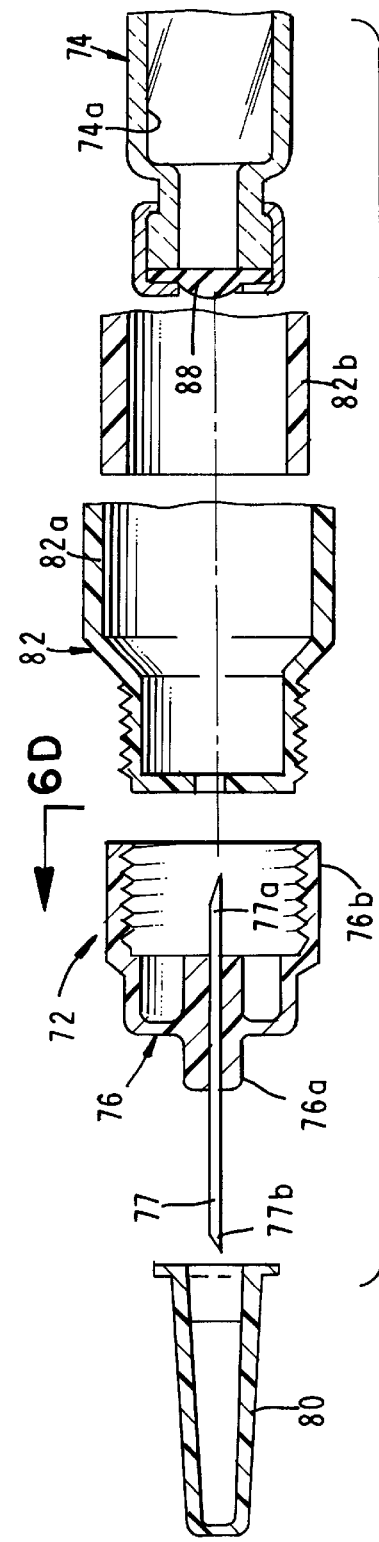

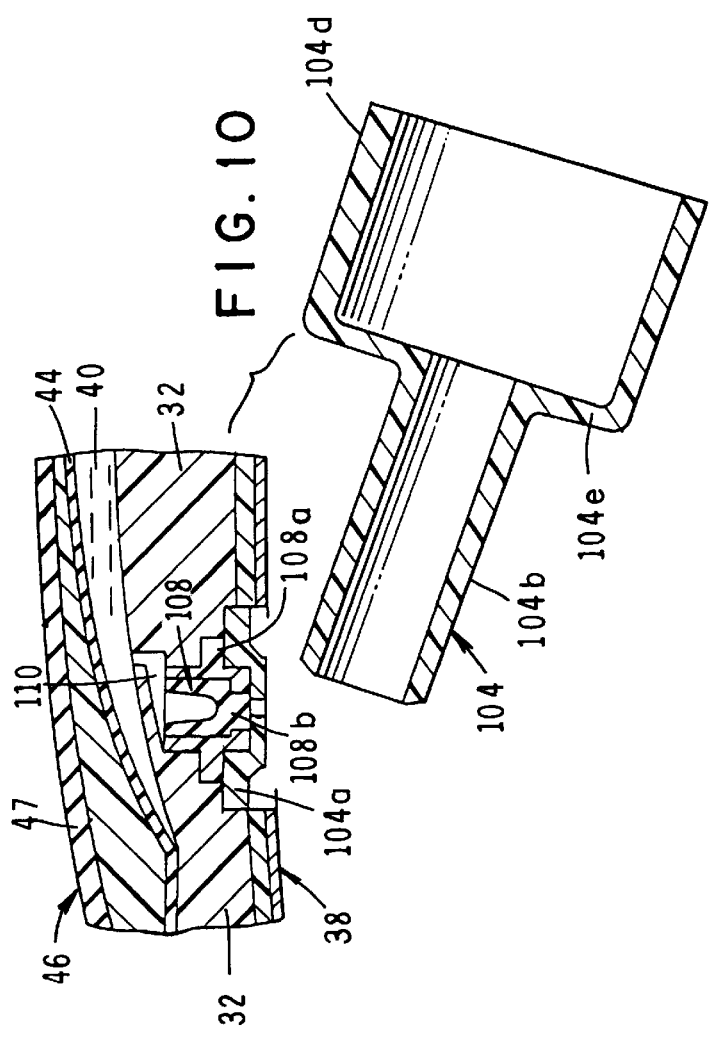
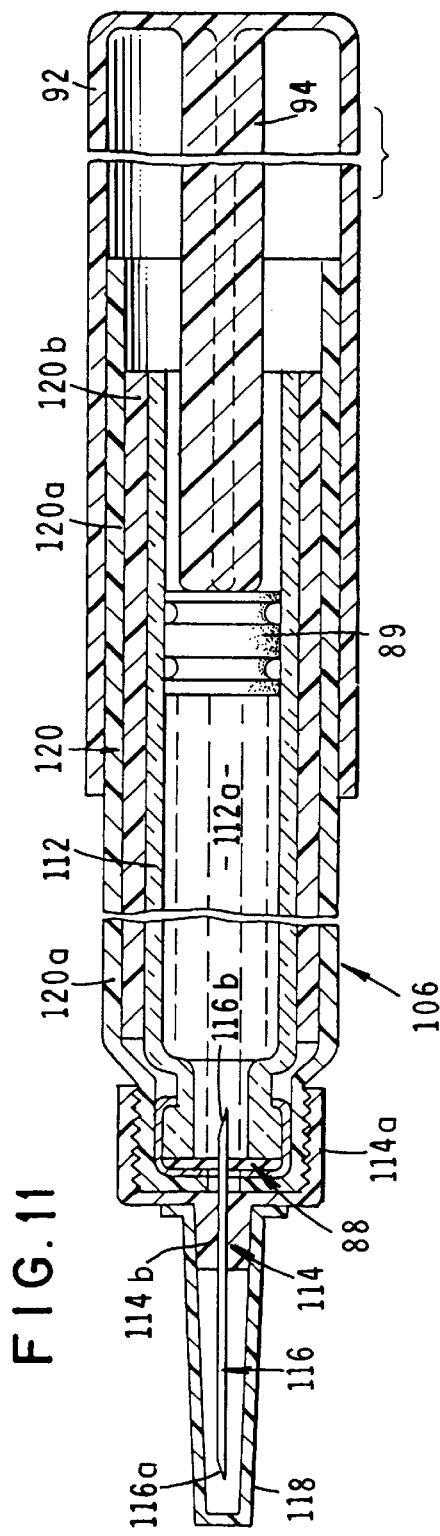
FIG. 10
FIG. 11

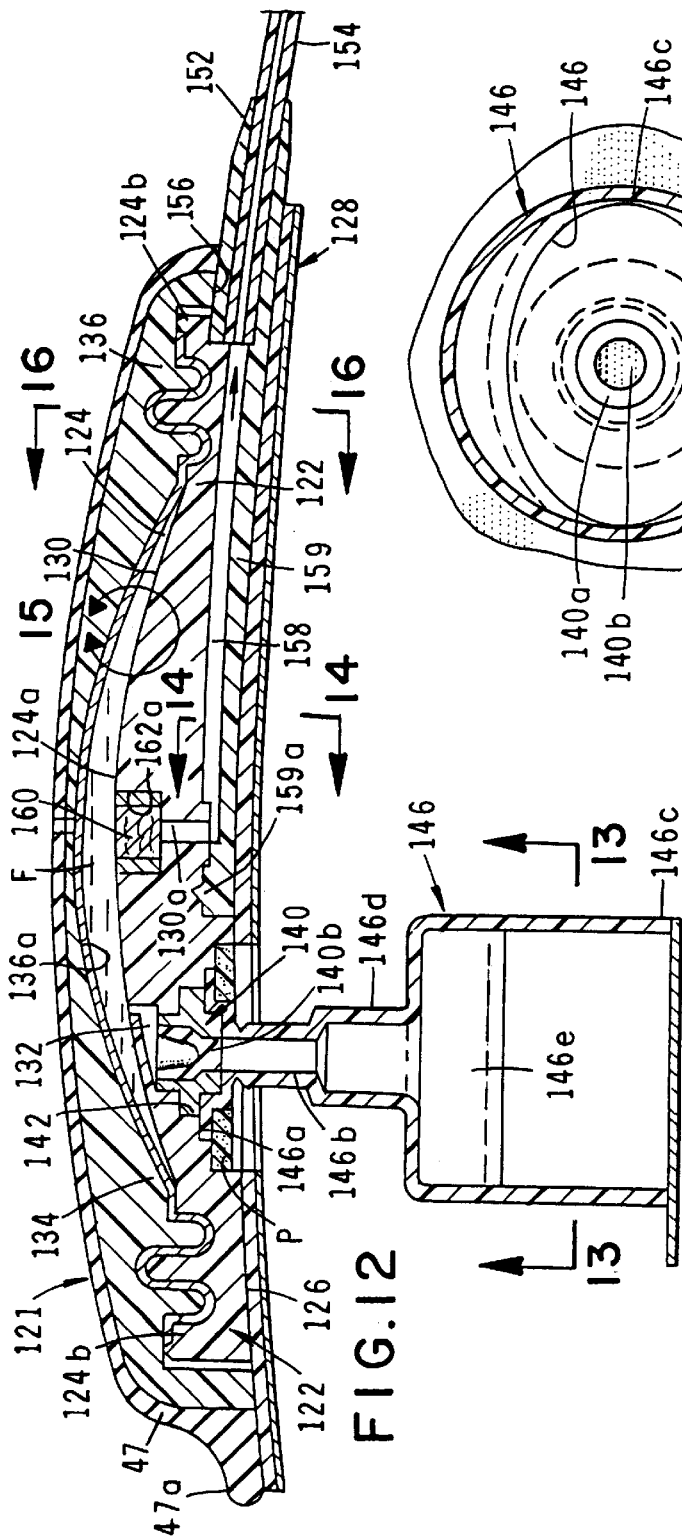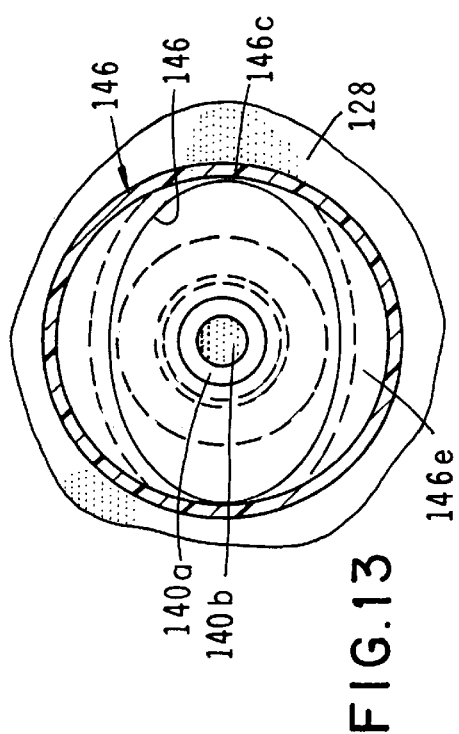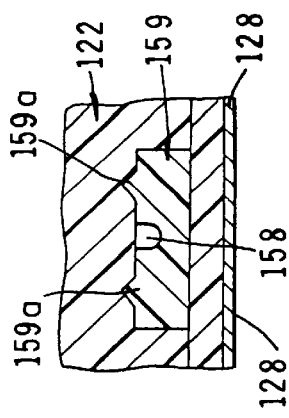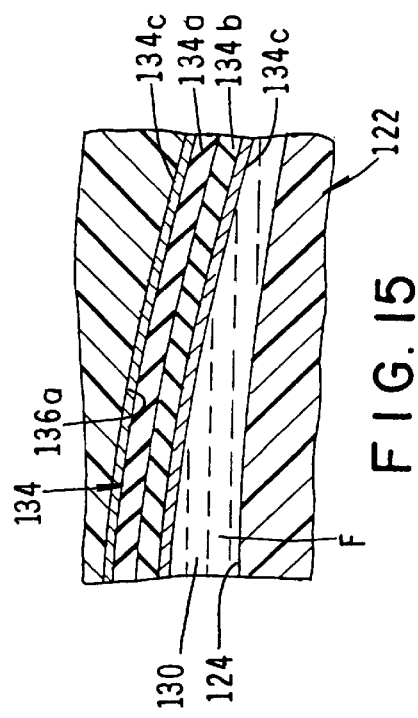

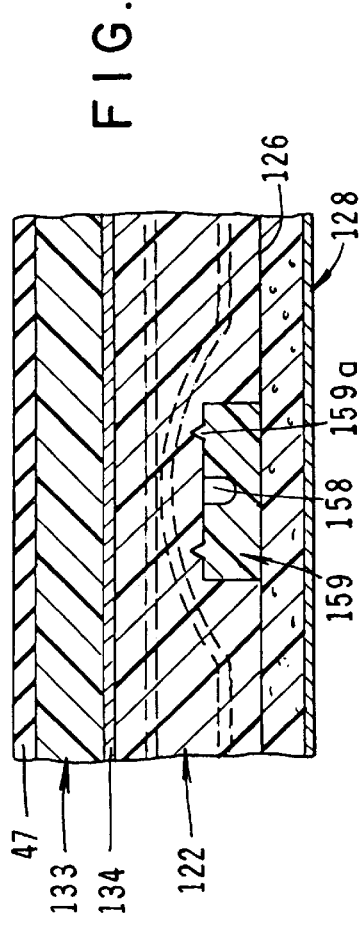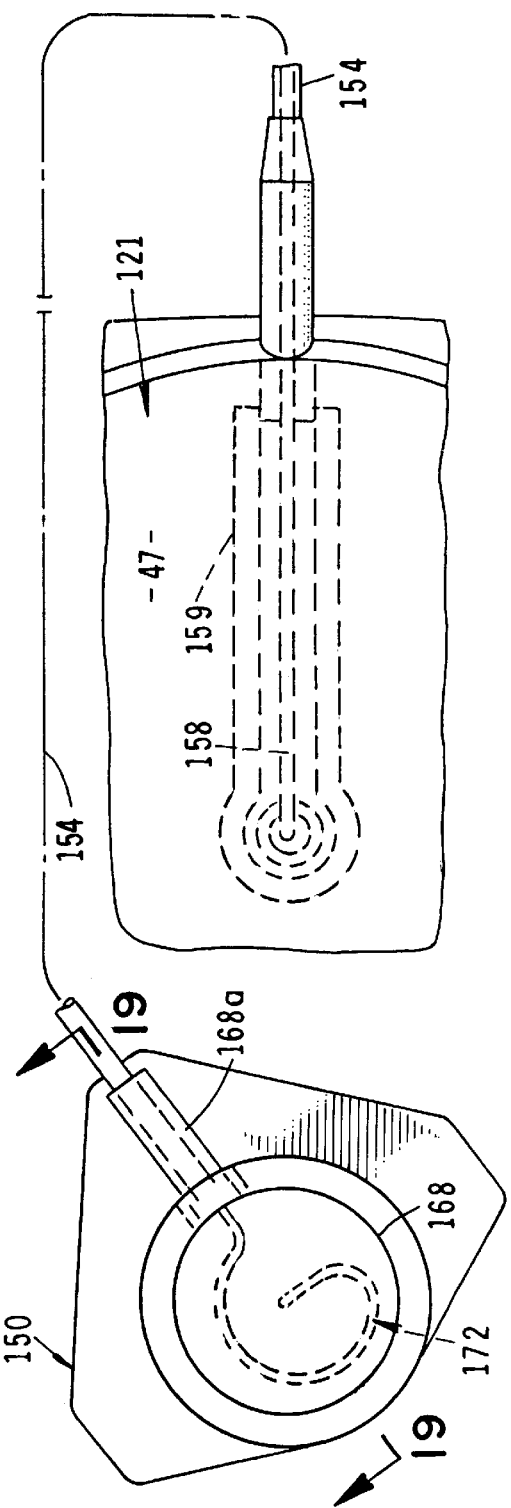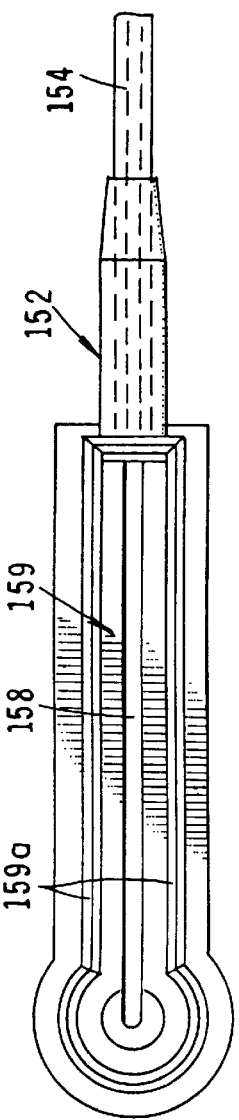

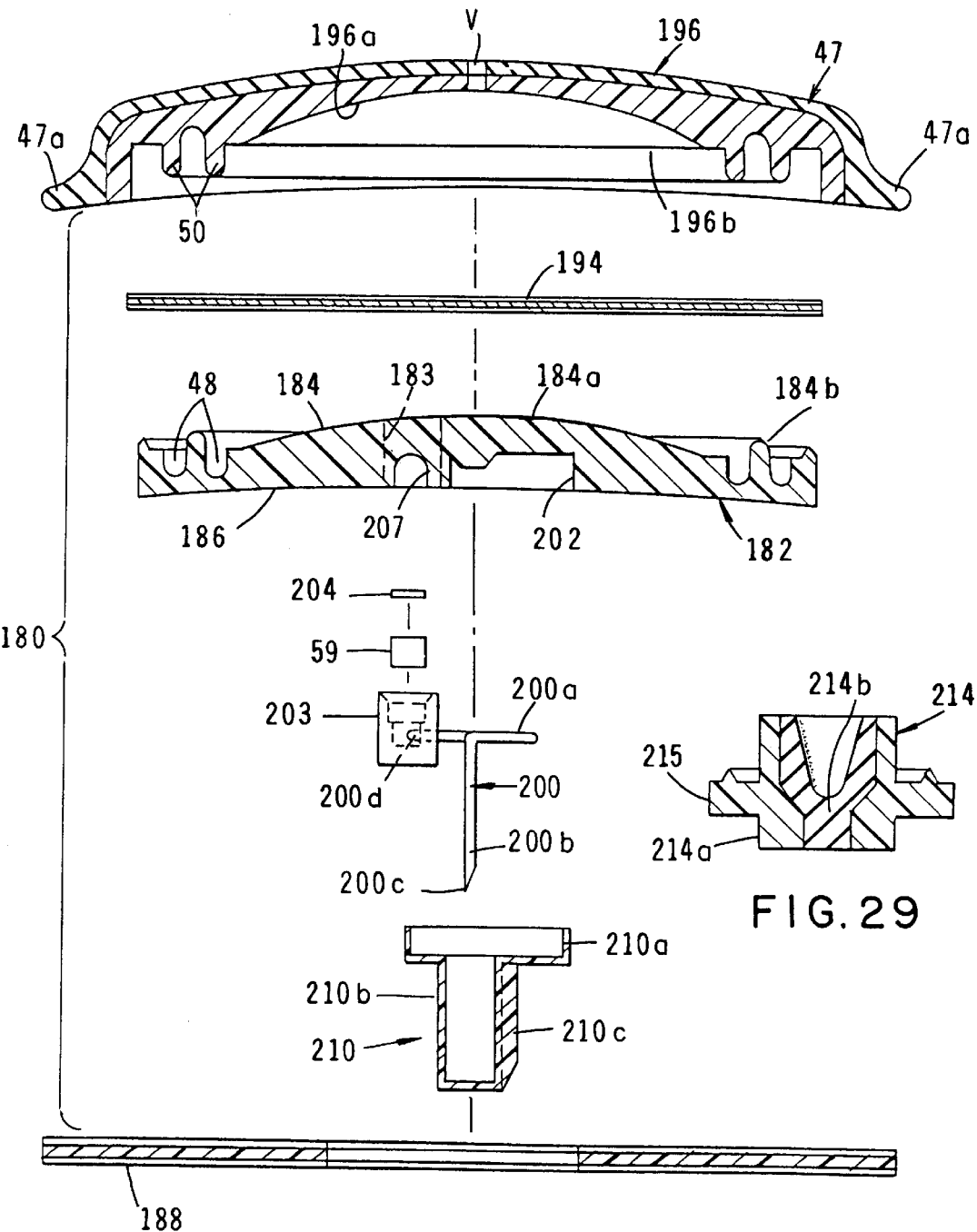

FLUID DELIVERY DEVICE WITH FILL ADAPTER

This is a Continuation-In-Part application of U.S. Ser. No. 08/606,090 filed Feb. 23, 1996 now U.S. Pat. No. 5,779,676, which is a Continuation-In-Part of application U.S. Ser. No. 08/541,184, filed Oct. 11, 1995 now U.S. Pat. No. 5,776,103.

BACKGROUND OF THE INVENTION

1. Field of the Invention

The present invention relates generally to fluid delivery devices. More particularly, the invention concerns an improved fluid delivery apparatus for precise subdermal delivery over time of medicinal liquids to an ambulatory patient, the device including novel reservoir filling means.

2. Discussion of the Prior Art

A number of different types of liquid dispensers for dispensing medicaments to ambulatory patients have been suggested. Many of the devices seek either to improve or to replace the traditional hypodermic syringe which has been the standard for delivery of liquid medicaments such as insulin solution.

Those patients that require frequent injections of the same or different amounts of medicament, find the use of the hypodermic syringe both inconvenient and unpleasant. Further, for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range much as the normally functioning pancreas would do by secreting a very low level of extremely fast-acting insulin at a basal rate into the blood stream throughout the day and night.

Consider the normal individual who doesn't have diabetes. A normal individual's cells require energy throughout the day just to maintain a basal metabolic rate. This energy is supplied to the cells by glucose that is transported from the bloodstream to the cells by insulin. When food is consumed, the blood glucose level rises and the pancreas responds by releasing a surge of fast-acting insulin. To mimic this natural process with individual injections, the individual would have to administer minuscule amounts of fast-acting insulin every few minutes throughout the day and night.

Conventional therapy usually involves injecting, separately, or in combination, fast-acting and slower-acting insulin by syringe several times a day, often coinciding with meals. The dose must be calculated based on glucose levels present in the blood. Slower-acting insulin is usually administered in the morning and evening to take advantage of longer periods of lower level glucose uptake. Fast-acting insulin is usually injected prior to meals. If the dosage of fast-acting insulin is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed study sponsored by the National Institutes of Health (NIH) investigated the effects of different therapeutic regimens on the health outcomes of insulin-dependent diabetics. This study revealed some distinct advantages in the adoption of certain therapeutic regimens. Intensive therapy that involved intensive blood glucose monitoring and more frequent administration of insulin by conventional means, for example, syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (for example, 0.3–3 mL. depending on body mass) over comparatively long periods of time (18–24 hours). As will be appreciated from the discussion which follows, the apparatus of the present invention is uniquely suited to provide precise fluid delivery management at a low cost in those cases where a variety of precise dosage schemes are of utmost importance.

An additional important feature of the apparatus of the present invention is the provision of a novel reservoir filling means disposed on the underside of the base.

Another feature of the improved apparatus of the invention comprises a novel reservoir fill adapter means for permitting the reservoir of the device to be filled by filling means of different configurations.

Still another important aspect of the invention is the provision of a novel, dynamically-mounted delivery connection.

Because the embodiments of the invention described herein comprise improvements to the devices described in U.S. Ser. No. 08/606,090 filed Feb. 23, 1997, application Ser. No. 08/606,090 is hereby incorporated by reference in its entirety as though fully set forth herein.

Also relative to a complete understanding of the present invention is an earlier filed application by the present inventor, which is identified by the Ser. No. 08/541,184. This application, which was filed on Oct. 11, 1995 is also incorporated by reference in its entirety as though fully set forth herein.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another useful liquid delivery device is that described in U.S. Pat. No. 5,514,097 issued to Knauer. The Knauer device comprises a medicament injection apparatus for subcutaneous or intramuscular delivery of a medicament which conceals the infusion needle behind a needle shroud. On apparatus activation, the needle is thrust forward, pushing the needle tip outside the needle shroud with enough force to puncture the skin. The needle is thus automatically introduced into the tissue at the proper needle/skin orientation. In the same action, the apparatus automatically dispenses an accurate pre-set dose.

U.S. Pat. No. 5,226,896 issued to Harris also describes a useful prior art device. This device comprises a multidose syringe having the same general appearance as a pen or mechanical pencil. The Harris device is specifically adapted to provide for multiple measured injections of materials such as insulin or human growth hormones.

Still another type of liquid delivery device is disclosed in U.S. Pat. No. 4,592,745 issued to Rex et al. This device is, in principle, constructed as a hypodermic syringe, but differs in that it enables dispensing of a predetermined portion from the available medicine and in that it dispenses very accurate doses.

The present invention seeks to significantly improve over the prior art by providing a novel fluid delivery device having unique filling and delivery means for filling the fluid reservoir of the device and for dispensing medicinal fluids therefrom.

SUMMARY OF THE INVENTION

It is an object of the present invention to provide an apparatus having a self-contained stored energy membrane for expelling fluids at a precisely controlled rate which is of a compact, laminate construction. More particularly, it is an object of the invention to provide such an apparatus which is of very low profile so that it can conveniently be used for the precise delivery of pharmaceutical fluids, such as insulin solution and the like, into an ambulatory patient at controlled rates over extended periods of time.

It is another object of the invention to provide an apparatus of the aforementioned character which is highly reliable and very easy-to-use by lay persons in a non-hospital environment.

Another object of the invention is to provide an apparatus of the character described in the preceding paragraphs which includes novel reservoir filling means for conveniently filling the fluid reservoir of the device.

Another object of the invention is to provide an apparatus of the character described which includes a novel fill adapter which permits filing of the reservoir of the apparatus only with filling means of a specific construction.

Another object of the invention is to provide an apparatus of the class described which further includes delivery means for precisely delivering medicinal fluids to the patient including the provision of a novel, dynamically mounted cannula assembly.

Another object of the invention is to provide an apparatus of the character described which, due to its unique construction, can be manufactured inexpensively in large volume by automated machinery.

Other objects of the invention are set forth in the co-pending United States application which are incorporated herein by reference and still further objects will become apparent from the discussion which follows.

BRIEF DESCRIPTION OF THE DRAWINGS

FIG. 1 is a bottom plan view of one form of the fluid delivery device of the present invention partly broken away to show internal construction.

FIG. 2 is a cross-sectional view taken along lines 2—2 FIG. 1.

FIG. 2A is an enlarged fragmentary, cross-sectional view of the area designated as 2A in FIG. 2.

FIG. 4 is an enlarged fragmentary, cross-sectional view of the area identified in FIG. 2 by the numeral 4.

FIG. 5 is a cross-sectional view taken along lines 5—5 of FIG. 4.

FIG. 6A is a side-elevational, cross-sectional view of the form of the syringe or fill device of the invention partially shown in FIG. 6 for use in filling the fluid reservoir of the embodiment of the delivery device shown in FIG. 2.

FIG. 6C is a fragmentary, exploded cross-sectional view of a portion of the fill device shown in FIG. 6A.

FIG. 10 is an exploded, cross-sectional view of the embodiment of the invention shown in FIG. 8 illustrating the breaking away of the fill adapter following the reservoir filling step.

FIG. 11 is an enlarged, cross-sectional view of the syringe or filling device of this latest form of the invention.

FIG. 12 is a cross-sectional view of still another form of fluid delivery device of the invention which includes an alternate type of infusion means.

FIG. 13 is a cross-sectional view taken along lines 13—13 of FIG. 12.

FIG. 14 is a cross-sectional view taken along lines 14—14 of FIG. 12.

FIG. 15 is a greatly enlarged, cross-sectional view of the area of FIG. 12 identified by the numeral 15.

FIG. 16 is a cross-sectional view taken along lines 16—16 of FIG. 12.

FIG. 17 is fragmentary top plan view of the infusion means of this latest form of the invention.

FIG. 18 is a fragmentary top plan view of a portion of the flow control element of the infusion means shown in FIG. 17.

FIG. 23 is an exploded, cross-sectional view of the embodiment of the invention shown in FIG. 22.

FIG. 29 is an enlarged, cross-sectional view of the fill port assembly of the embodiment of the invention shown in FIG. 26.

DESCRIPTION OF THE INVENTION

Figures 3, 3A:
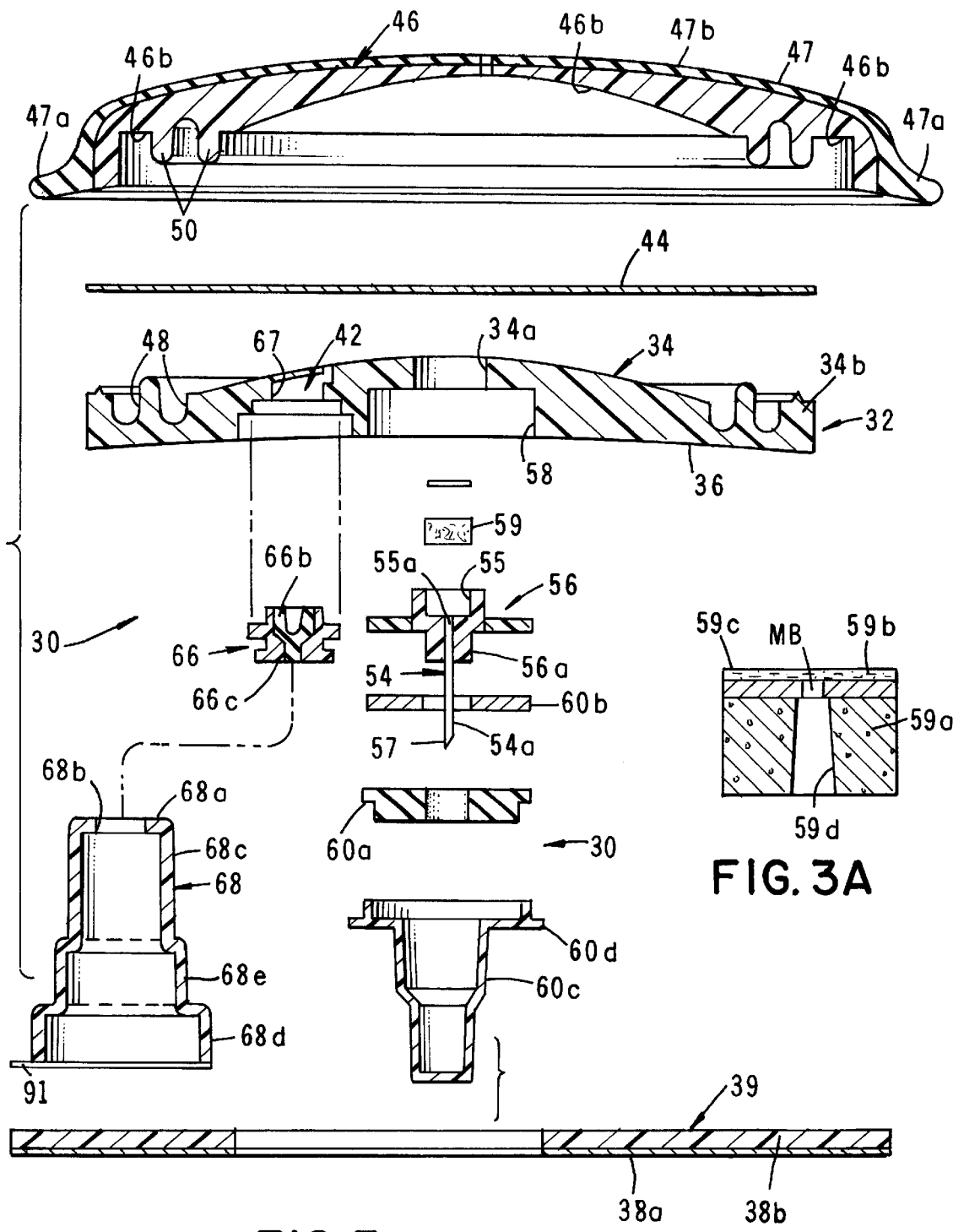
FIG. 3 is an exploded, cross-sectional view of the device shown in FIG. 2.
FIG. 3A is an enlarged, cross-sectional view of an alternate form of flow rate control element of the invention.

Referring to the drawings and particularly to FIGS. 1 through 6, one form of the fluid delivery device of the invention is there shown and generally designated by the numeral 30. This form of the invention, which is specially designed for subdermal infusion of selected medicaments, comprises a base 32 having an upper surface 34 including a generally dome shaped central portion 34a and a peripheral portion 34b circumscribing central portion 34a. As best seen in FIGS. 2 and 3, base 32 is also provided with a lower surface 36 to which a patient interconnection means or adhesive pad assembly 38 is connected. Pad assembly 38, which comprises a foam tape having adhesive on both sides, functions to releasably interconnect the device to the patient so as to hold it securely in place during the medicament delivery step. A peal-away member 38a covers the lower surface of the pad 38b.

A stored energy means cooperates with the upper surface 34 of base 32 to form a reservoir 40 (FIG. 2) having an inlet port assembly 42, which, in a manner presently to be described, is adapted to cooperate with a filling means for filling reservoir 40 with the medicinal fluid to be infused into the patient. The stored energy means is here provided in the form of at least one distendable membrane 44 which is superimposed over base 32. Membrane 44 is distendable as a result of pressure imparted on the membrane by fluids introduced into reservoir 40 via inlet port assembly 42 (FIG. 2). As membrane 44 is distended in the manner shown in FIG. 2, internal stresses will be established, which stresses tend to move the membrane toward a less distended configuration and in a direction toward upper surface 34 of base 32. Membrane 44 can be constructed from a single membrane or from multiple membranes which are overlayed to form a laminate construction.

Provided within the reservoir of the device, which is defined by the upper surface 34 of the base and a concave surface 46a of a cover means for covering the distendable membrane, is ullage defining means for providing ullage within the reservoir and for engagement with membrane 44 as the membrane moves toward its less distended starting configuration. The ullage defining means here comprises the previously identified, dome shaped central portion 34a of base 32. When the distendable membrane after being distended, tends to return toward its less distended configuration, fluid contained within the reservoir 40 will flow uniformly outwardly of the reservoir through the infusion means of the invention for infusing the medicinal fluids contained within the reservoir into the patient.

Superimposed over base 32 is the cover means, shown here as a rigid cover 46 which functions, through the use of novel sealing means, to sealably enclose membrane 44. The sealing means here comprises a pair of generally circular grooves 48 formed in peripheral surface 34b of base 32 and a pair of cooperating, generally circular shaped rim like protuberances 50 formed on the peripheral lower surface 46b of the cover 46. Protuberances 50 are receivable within grooves 48 in the manner shown in FIG. 2 and function to sealably clamp distendable membrane 44 between the cover and the base. A soft elastomer covering 47 is provided over the upper surface of cover 46 to make the device more patient friendly. More specifically, as shown in FIG. 2, covering 47 includes soft edges and corners 47a which prevent the edges and corners of the device from jabbing into the patient's flesh. Cover 47 also includes a soft, pliable overcover 47b. While several materials can be used for covering 47, materials such as a material sold under the name and style "Santoprene" by The Monsanto Company of St. Louis, Mo. has proven satisfactory for this purpose.

Examples of materials found particularly well suited for the construction of distendable membrane 44 include: silicone polymers (polysiloxanes) (high performance silicone elastomers made from high molecular weight polymers with appropriate fillers added). These materials are castable into thin film membranes and have high permeability (which allows maximum transport of vapor and gas), high bond and tear strength and excellent low temperature flexible and radiation resistance. Additionally, silicone elastomers retain their properties over a wide range of temperatures ($-80°$ to $200°$ C.) are stable at high temperatures, and exhibit tensile strengths up to 2,000 lb./in$^2$ elongation up to 600%. Another suitable material for the stored energy membrane is natural and synthetic latex.

Manufacturers of materials suitable for use in construction of the distendable membrane include Dow Chemical, General Electric, B.P. Polymers, Mobay Chemical, Shell Oil Corp., Petrarch Systems, DuPont, Concept Polymers, Goodyear and Union Carbide Corp.

With respect to the structural cover 46 and base 32, these components can also be produced from a variety of materials including one of several polymer groups. The degree of hardness of these materials can range from soft, resilient or rigid, and the following polymers can be employed: Polypropylene (PP), Ultra high molecular weight polyethylene (UHMW PE), High density polyethylene (HDPE), Polyvinylidene Fluoride (PVDF), Ethylenevinyl acetate (EVA), Styrene Acrylonitrile (SAN), Polytetrafluoroethylene (PTFF). A suitable source of these materials is Porex Technologies of Fairburn, Ga. It is to be understood that other suitable materials well known to those skilled in the art can also be used, including a material sold by B.P. Chemicals International of Cleveland, Ohio, under the name and style "Barex". This material is a clear rubber modified Acroylonitrile Copolymer which has wide application in the packaging industry because of its superior gas barrier, chemical resistance and extrusion (thermoforming) and injection molding capabilities.

Referring particularly to FIGS. 2 and 3, the infusion means of this latest form of the invention for subdermal infusion of medicaments into the patient, can be seen to include, a downwardly extending hollow cannula 54 which is carried by a support member 56 that is received within a cavity 58 formed in base 32. Support member 56 also functions to support, within a cavity 55, flow control means for controlling the rate of fluid flow from reservoir 40 toward hollow cannula 54. This flow control means is here provided as a porous rate control frit 59 which can be constructed from a micro porous metal such as stainless steel. The frit can also be constructed from a porous ceramic or plastic material.

Referring to FIG. 3A, an alternate form of rate control assemblage is there shown. This unique assemblage is receivable within cavity 55 and comprises a plastic base 59a, a thin flow control wafer 59b superimposed over base 59a and a thin filter member 59c superimposed over wafer 59b. Wafter 59b includes an extremely small laser drilled aperture or microbore "MB". Base 59a, which includes a central fluid passageway 59d, can be constructed of numerous materials such as polycarbonate, acrylic, polypropylene and the like. Wafer 59b is preferably constructed from materials such as plastic films including polyester material. Filter member 59c is preferably constructed from materials such as polysolfone and polypropylene but other porous materials can also be used.

Hollow cannula 54 has an inlet end 55a and an outlet end 57 formed in a needle-like segment 54a which extends generally perpendicularly downward from the lower surface 36 of base 32. To protect cannula 54 from damage, a protective cover assembly 60 surrounds the cannula. As best seen in FIG. 3, cover assembly 60 includes spacer member 60a, a potting material 60b, and a sheath member 60c. At time of use the sheath member 60c can be broken away from the base portion 32 in the manner shown in the phantom lines of FIG. 2. For this purpose, a serration line 62 is formed between the body of the sheath member and a connector collar 60d which functions to interconnect the cover assembly 60 with the base 32.

Figure 6:
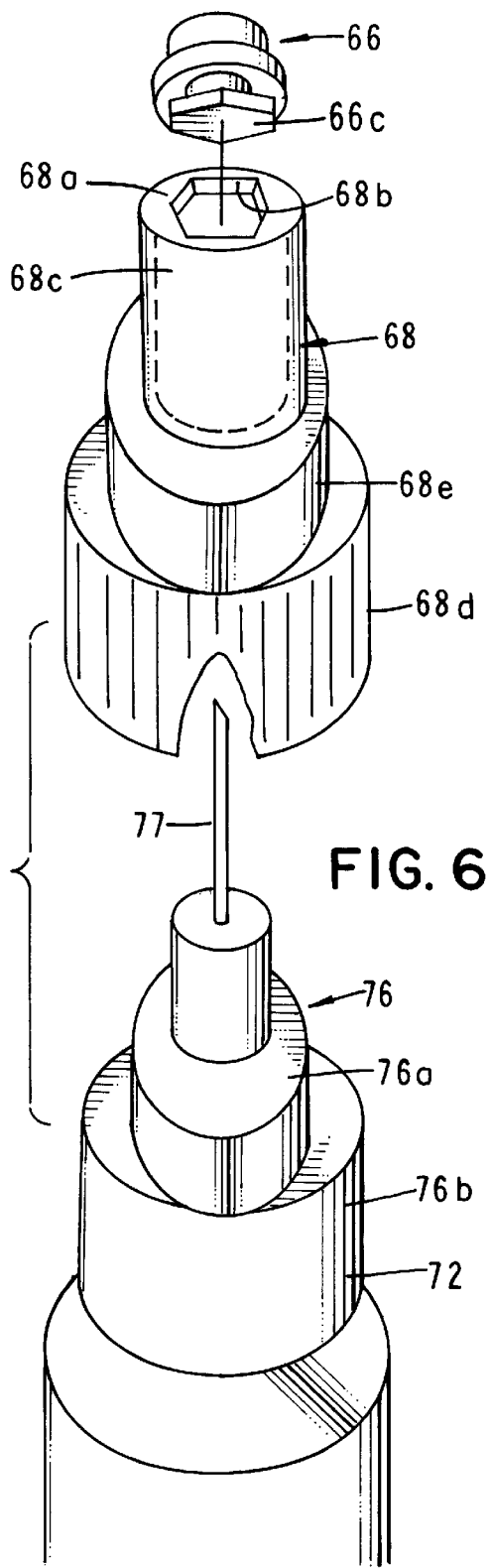
FIG. 6 is a generally perspective exploded view of one form of filling adapter of the invention and one type of filling syringe which is mateable with the filling adapter to permit controlled filling of the fluid reservoir of the device.
Figure 6B:
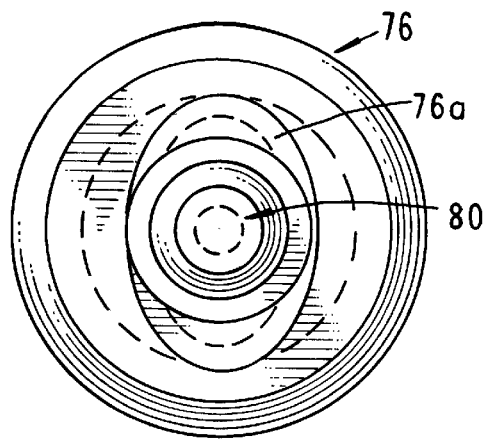
FIG. 6B is a view taken along lines 6B—6B of FIG. 6A.
Figure 6D:
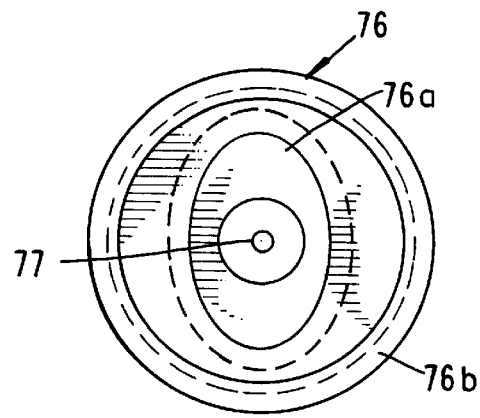
FIG. 6D is a view taken along lines 6D—6D of FIG. 6C.

Referring particularly to FIGS. 4, 5, and 6, one form of the novel filling means of the present invention is there illustrated. As previously mentioned, the filling means functions to controllably fill reservoir 40 with the medicinal fluid which is to be infused into the patient. In the present form of the invention, the filling means comprises a septum assembly, a filling syringe assembly and a novel fill adapter assembly. As best seen in FIG. 4, septum assembly 66 is sealably disposed within a fill port 67 formed in the intermediate portion of base 32 (see also FIGS. 2 and 3). Septum assembly 66 includes a septum housing 66a which is receivable within fill port 67 and an elastomeric, pierceable core 66b which is sealably disposed within an opening formed in septum housing 66a.

As shown in FIGS. 4, 5, and 6 septum housing 66a includes a non-circular, generally oblong shaped connector base 66c which functions to interconnect the fill adapter 68 of the invention with the septum assembly 66. Referring particularly to FIGS. 5 and 6, it is to be observed that fill adapter 68 includes connector means, comprising a base wall 68a having a non-circularly shaped opening 68b formed therein for receiving base 66c of the septum housing. With this construction, when the fill adapter is mated with the septum assembly and then rotated ninety degrees, the fill adapter will be securely located in place as shown in FIGS. 4 and 5.

As indicated in FIGS. 3, 4, and 6, fill adapter 68 includes an upper wall portion 68c, a lower wall portion 68d, and an intermediate wall portion 68e. For purposes presently to be described, intermediate wall portion 68e is generally oval shaped in cross section (see also FIGS. 5 and 6).

Also forming a part of the filling means of the present invention is a filling syringe assembly 72 which, as best seen in FIG. 6A, includes a vial like container 74 having a fluid reservoir 74a, a needle housing 76 closing fluid reservoir 74, and a double ended piercing needle 77 carried by needle housing 76. As indicated in FIG. 6, the collar portion 76a of needle housing 76 is also oval shaped and when correctly indexed is adapted to be closely received within oval shaped wall section 68e of fill adapter 68. With this novel arrangement, it is apparent that a conventional syringe having a circular shaped needle housing cannot be inserted into adapter 68 since the wall located between wall section 68d and 68e, would act as a stop to prevent complete insertion of the conventional syringe assembly into the adapter so that the needle portion thereof could pierce the elastomeric core 66b of the septum assembly 66. Also forming a part of the filling syringe of the present form of the invention is a needle protector cap 80 which is of the configuration shown in FIG. 6C and is adapted to be received over the piercing needle 77 to protect it from damage and contamination.

Turning particularly to FIGS. 6A and 6C, filling syringe 72 can be seen to comprise, in addition to the previously mentioned vial 74, needle housing 76, needle 77 and closure cap 80, an elongated housing assembly 82 which houses medicament vial 74. Housing assembly 82 includes a hollow housing 82a and a spacer sleeve 82b which insures a close fit of vial 74 within hollow housing 82a. As shown in FIG. 6A, the fluid reservoir 74a of vial 74 is sealed at one end by a pierceable closure septum 88 and is seated proximate its opposite end by an elastomeric plunger 89 which is telescopically movable along the length of reservoir 74a to expel fluid therefrom via needle 77. The needle housing 76, which supports needle 77 includes an internally threaded collar 76b which enables threadable interconnection with housing 82a in the manner shown in FIG. 6A so that the inwardly extending portion 77a of the needle will pierce closure septum 88 upon interconnection of the needle housing with hollow housing 82a. With this construction, portion 77b of needle 77 extends forwardly to enable the needle to pierce septum core 66b of septum assembly 66 upon mating the syringe assembly with adapter 68.

In using filling syringe assembly 72 to fill reservoir 40 of the delivery portion of the device, a protective cover 91 is pulled away from the bottom of adapter 68 (FIG. 4) and protective cap 60 is removed in the manner shown by the phantom lines of FIG. 2. Next, needle housing 76 along with needle 77 are telescopically inserted into adapter 68. By rotating the filling syringe to a position where oval collar 76a indexes with oval shaped wall section 68e of the adapter, the syringe can be urged inwardly of the adapter causing needle to pierce septum core 66b thereby placing reservoir 40 of the delivery device in fluid communication with reservoir 74a of medicament vial 74 (see the phantom lines of FIG. 2).

Also forming an important part of the filling syringe assembly 72 of the present form of the invention, pusher sleeve 92 which is telescopically receivable over housing 82 in the manner shown in FIG. 6A. Disposed internally of sleeve 92 is a pusher rod 94 which is adapted to engage plunger 89 and move it longitudinally of reservoir 74a as the pusher sleeve is moved from the first extended position shown in FIG. 6A to a position wherein a substantial portion of housing 82 is encapsulated within the sleeve. As sleeve 92 is moved toward the second position, plunger 89 will move inwardly of reservoir 74a causing fluid contained therein to flow toward reservoir 40 of the delivery device via hollow needle 77.

Figure 7A:
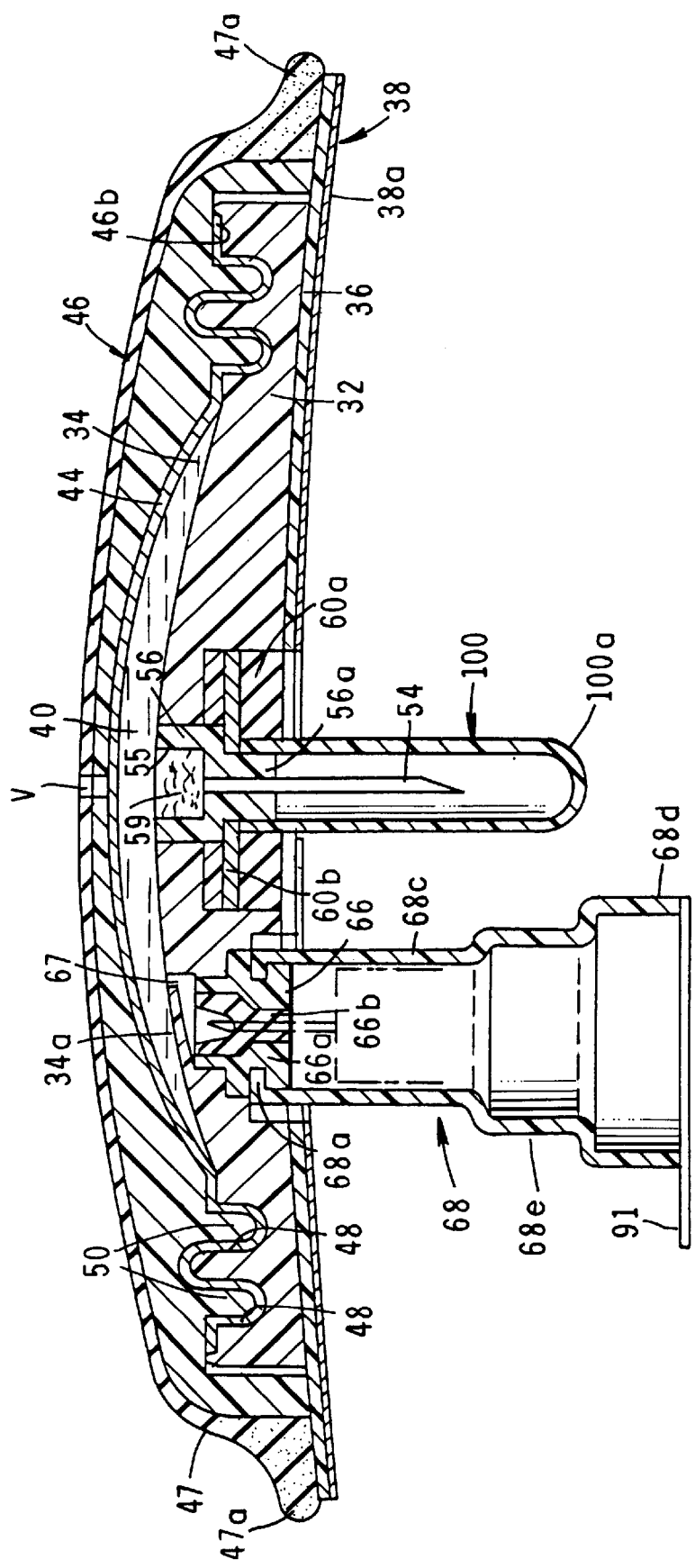
FIG. 7A is a cross-sectional view of an alternate form of fluid delivery device of the invention.
Figure 7B:
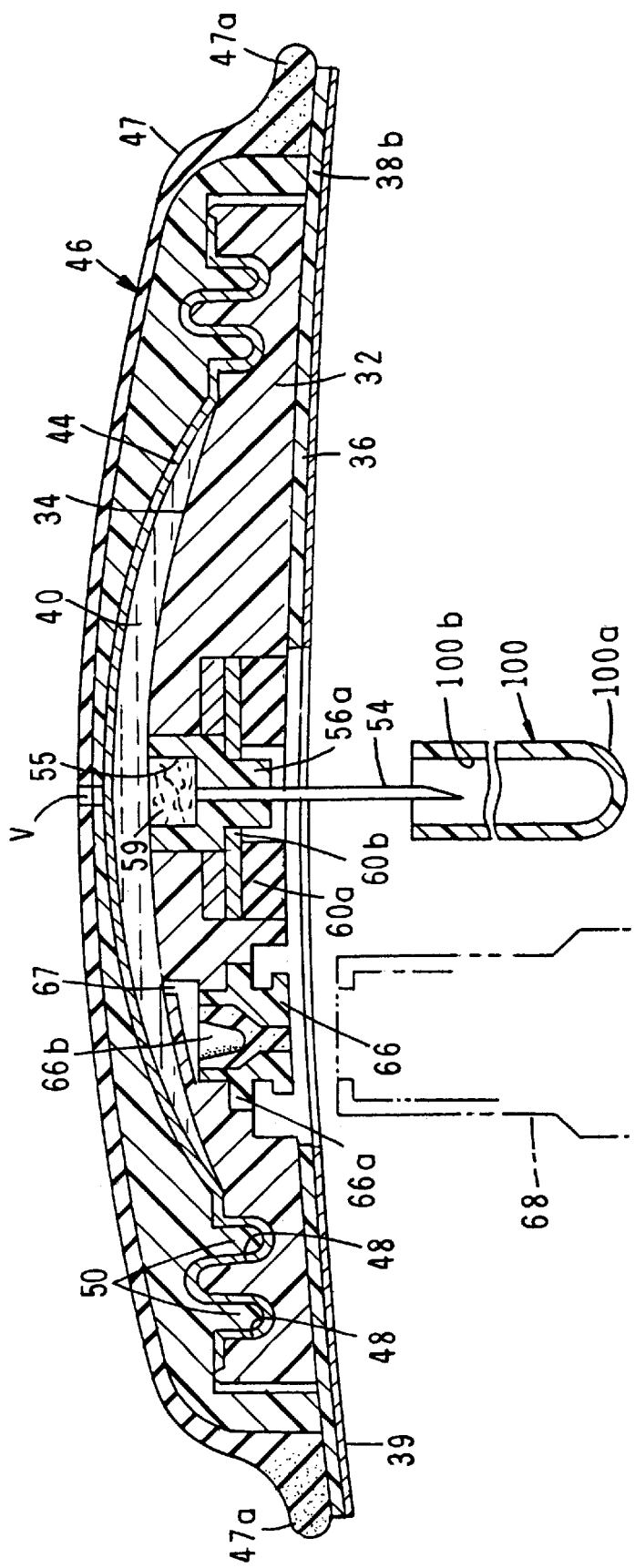
FIG. 7B is an exploded, cross-sectional view of the fluid delivery device shown in FIG. 7A illustrating the removal from the device of the fill adapter and the cannula cover.

Turning next to FIGS. 7A and 7B, an alternate form of the fluid delivery device of the invention is there shown. This device is quite similar to that shown in FIGS. 1 through 6A and like numerals are used in FIGS. 7A and 7B to identify like components. The primary difference between the earlier described embodiment and the embodiment of FIGS. 7A and 7B resides in the differently configured cannula protective sheath identified in FIGS. 7A and 7B by the numeral 100. As best seen in FIG. 7B sheath 100 is generally cylindrical in shape and is smaller in diameter than sheath 60 of the earlier described embodiment. The outboard end of sheath 100 is closed by a generally hemispherically shaped closure wall 100a and the inboard end 100b is open. The inside diameter of open end 100b is such that it is closely receivable over the needle boss 56a of cannula assembly 56 to create an interference fit therewith. With this construction, when the reservoir of the device is filled and the adapter 68 removed from the base in the manner shown by the phantom lines of FIG. 7B, protective sheath 100 can be removed to expose cannula 54 by merely exerting a downward, separating force on the sheath body sufficient to separate it from boss 56a.

Referring to FIGS. 8 through 11, still another form of the fluid delivery device of the invention is there shown. This device is also very similar to that shown in FIGS. 1 through 6A and like numerals are used in FIGS. 8 through 11 to identify like components. The primary difference between the earlier described embodiments and the embodiment of FIGS. 8 through 11 resides in the differently configured filling adapter 104 and the filling means or filling syringe assembly 106 which mates therewith. As previously mentioned, the filling means functions to controllably fill the reservoir of the delivery portion of the device with the medicinal fluid which is to be infused into the patient. In this latest form of the invention, the filling means comprises a septum assembly 108 which is sealably disposed within fill port 110 formed in the intermediate portion of base 32 (see FIG. 8). Septum assembly 108 is quite similar to the previously described septum assembly 66 and includes a septum housing 108a which is receivable within fill port 110 and an elastomeric, pierceable, non-coring core 108b which is sealably disposed within an opening formed in septum housing 108.

Figure 8:
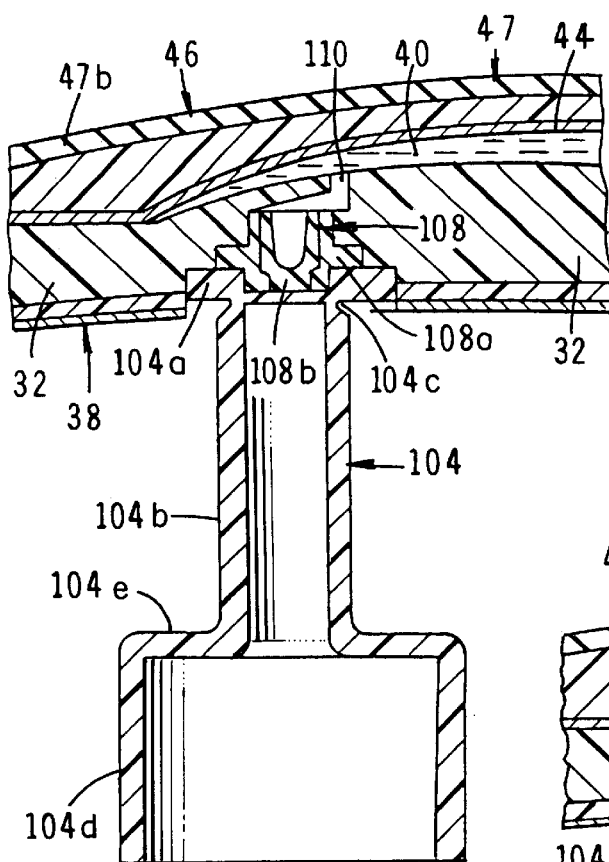
FIG. 8 is a fragmentary, cross-sectional view of another embodiment of the fluid delivery device of the invention showing a fill adapter of a slightly different configuration.

Referring to FIG. 8, it is to be noted that fill adapter 104 includes a connector flange 104a which is fixedly connected as by adhesive bonding or the like to base 32 proximate fill port 110. Disposed between flange 104a and a cylindrical body section 104b is a serration 104c which permits body section 104b to be easily broken away from flange 104a leaving a smooth undersurface which is generally parallel with the lower surface of base 32 (see FIG. 10). Integrally formed with body section 104b is a cup-like syringe receiving section 104d which is adapted to telescopically receive the upper portion of syringe assembly 106 in the manner shown in FIG. 9. It is to be understood that, although the fill adapter is shown interconnected with the lower surface of the base of the device, it could also be connected to the side surfaces or to any other convenient surface.

Figure 9:
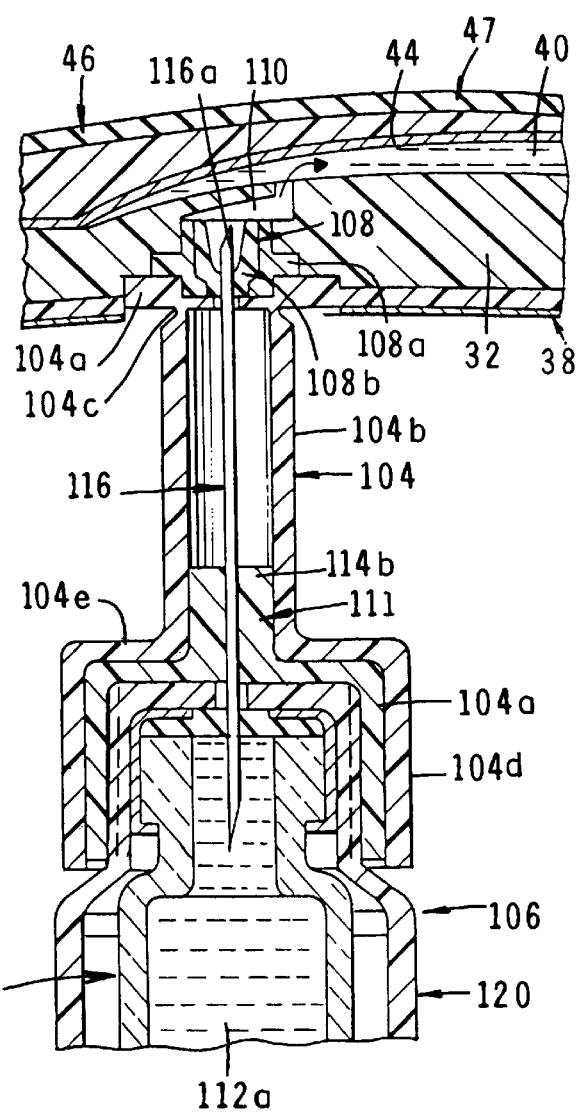
FIG. 9 is a fragmentary, cross-sectional view similar to FIG. 8 but showing the filling syringe of this alternate embodiment mated with the alternate form of fill adapter.

Turning next to FIG. 11, the filling means or syringe assembly 106 is of similar construction to the previously described filling syringe 72 and includes a container or vial 112 having a fluid reservoir 112a, a needle housing 114, and a double ended piercing needle 116 carried by needle housing 114. As indicated in FIG. 11, the threaded collar 114a of the needle housing 114 is of a size and shape adapted to be closely received within cylindrically shaped wall section 104d of fill adapter 104 while end 114b of the needle housing is adapted to be closely receivable within section 104b of the fill adapter (FIG. 9). With this novel arrangement, the outboard end 114b of the needle housing is receivable within section 104b of the fill adapter as the collar portion 114b of the needle housing is inserted into adapter portion 104d. As illustrated in FIG. 9, insertion of the syringe assembly 106 into adapter 104 causes the needle portion of the syringe assembly thereof to pierce the elastomeric core 108b of the septum assembly 108 thereby opening fluid communication between reservoir 112a of the fill vial and the outlet 116a of hollow cannula 116. Also forming a part of the filling syringe of the present form of the invention is a needle protector cap 118 which is of the configuration shown in FIG. 11 and is adapted to be received over the piercing needle 116 to protect it from damage and contamination.

In addition to the previously mentioned needle housing 114, needle 116 and closure cap 118, the filling syringe assembly 106 also includes a housing assembly 120 which houses vial 112.

As before, reservoir 112a of vial 112 is sealed at one end by a septum assembly 88 and is sealed at its opposite end by an elastomeric plunger 89 which is telescopically movable along the length of reservoir 112a to expel fluid from the reservoir through hollow cannula 116. Septum assembly 88 and plunger 89 are of the construction as previously described. Needle housing 114, is threadably connected to hollow housing 120a and carries hollow needle 116 in the manner shown in FIG. 11 so that the inwardly extending portion 116b thereof will function to pierce the septum core 88 of the vial assembly when the needle housing is threadably coupled with hollow housing 120a. To insure a snug fit, spacer sleeve 120b is disposed between vial 112 and the interior wall of hollow housing 120a in the manner shown in FIG. 11.

In using filling syringe 106 to fill reservoir 40 of the delivery portion of the device, protective cap 118 is first removed and the needle housing 114 along with needle 116 are telescopically inserted into adapter 104. As the syringe assembly is urged inwardly of the adapter, needle 116 will pierce pierceable core 108b of the septum assembly thereby placing reservoir 40 of the delivery device in fluid communication with reservoir 112a of medicament vial 112. As the needle pierces core 108b, portion 114a of the needle housing will seat against a shoulder 104e formed on adapter 104 and portion 114b will be received within portion 104b of the adapter.

Also forming a part of the filling syringe assembly 106 is the previously described pusher sleeve 92 which is telescopically receivable over housing 120a. Disposed internally of housing 120a is a pusher rod 94 which, as before, is adapted to engage plunger 89 and move it longitudinally of reservoir 112a as the pusher sleeve is moved from the first extended position shown in FIG. 11 to a second position wherein a substantial portion of housing 120a is encapsulated within the sleeve. As sleeve 92 is moved toward the second position, plunger 89 will move inwardly of reservoir 112a causing fluid to flow toward reservoir 40 of the delivery device via hollow needle 116.

Turning next to FIGS. 12 through 20, still another form of the fluid delivery device of the invention is there shown and generally designated by the numeral 121. This device is similar in many respects to that shown in FIGS. 1 through 6A and like numerals are used in FIGS. 12 through 20 to identify like components. The primary difference between the earlier described embodiment and the embodiment of FIGS. 12 through 20 resides in the differently configured fill adapter and the totally different infusion means of the invention for infusing medicinal fluids into the patient. The details of construction of both of these novel features of the invention will presently be described.

As best seen in FIG. 12, this latest form of the invention comprises a base 122 having an upper surface 124 including a generally dome shaped central portion 124a and a peripheral portion 124b circumscribing central portion 124a. Base 122 is also provided with a lower surface 126 to which a patient interconnection means or adhesive pad assembly 128 of the general character previously described is connected.

A stored energy means cooperates with the upper surface 124 of base 122 to form a reservoir 130 having an inlet port 132, which is adapted to cooperate with a filling means of this latest form of the invention for filling reservoir 130 with the medicinal fluid to be infused into the patient. The stored energy means is here provided in the form of a laminate construction or assemblage 134 which is made up of a first and second distendable membrane 134a and 134b (FIG. 15) which are here shown as coated, for specialized biocompatibility purposes, with a flurosilicone barrier material 134c. Membrane assemblage 134 is distendable as a result of pressure imparted on the membrane by fluids "F" introduced into reservoir 130 through inlet port 132. As the membrane assemblage is distended in the manner shown in FIG. 12, internal stresses will be established, which stresses tend to move the assemblage toward a less distended configuration and in a direction toward base 122.

Provided within the reservoir of the device, which is defined by the upper surface of the base and a concave surface 136a of a cover means for covering the distendable membrane, is ullage defining means for providing ullage within the reservoir and for engagement with membrane assembly 134 as the assembly moves toward its less distended starting configuration. As before, the ullage defining means here comprises the dome shaped central portion 124a of base 122. When the distendable membrane assemblage, after being distended, tends to return toward its less distended configuration, fluid contained within the reservoir 130 will flow uniformly outwardly of the reservoir through the novel infusion means of the invention for infusing medicinal fluids into the patient.

Superimposed over base 122 is the cover means, shown here as a rigid cover 136 which is of the same general character as previously described and through the use of novel sealing means, to sealably enclose membrane 134. The sealing means is identical to that previously described in connection with the embodiment of the invention shown in FIGS. 1 through 6.

Referring particularly to FIGS. 12 and 13, the novel filling means of this latest form of the invention can be seen to comprise a septum assembly 140 which is sealably disposed within a fill port 142 formed in the intermediate portion of base 122 (see FIG. 12). Septum assembly 140 is somewhat similar to septum assembly 66 and includes an elastomeric pierceable core 140b which is sealably disposed within a core housing 140a.

As best seen in FIG. 12, septum assembly 140 is disposed proximate the upper end of a fill adapter 146 which in this form of the invention is connected to base 122 by means of a suitable potting compound "P" which fills the lower portion of fill port 142 and functions to hold a flange 146a formed on fill adapter 146 in position within the fill port.

As in the earlier described embodiments, fill adapter 146 includes a first reduced diameter portion 146b, a lower wall portion 146c, and an intermediate wall portion 146d. As indicated in FIG. 13, wall portion 146c defines, proximate its upper region 146e, a generally oval shaped opening 147 which, as before, will accept only filling syringes having the correct oval mating configuration.

Also forming a part of the filling means of this latest form of the invention is the previously illustrated and described filling syringe 72 (FIG. 6) which is identical in construction and use to that previously described and includes an oval shaped collar that is of a configuration that can be closely received within oval shaped opening 147 of fill adapter 146 (see also FIG. 6A). As before with this arrangement, a conventional syringe having a circular shaped needle housing cannot be fully inserted into adapter 146 since portion 146e would act as a stop and prevent insertion of the conventional syringe assembly into the adapter in a manner such that the needle portion thereof could pierce the elastomeric core 140a of the septum assembly.

As previously mentioned, the infusion means of the present form of the invention is totally different in construction and operation from that shown in FIGS. 1 through 11. More particularly, this novel infusion means here comprises an administration set having a subcutaneous infusion device 150 (FIG. 17) and connector means for operably interconnecting device 150 with the fluid reservoir 130 of the fluid delivery device. As best seen in FIGS. 16, 17, and 18, the connector means here comprises a connector boss 152 and a length of tubing 154 which interconnects device 150 with boss 152 (FIG. 17). Connector boss 152 is sealably received within a connector boss receiving port 156 formed in base 122 and cover 136 (FIG. 12) in a manner so as to place tubing 154 in communication with a flow passageway 158 formed in a flow plate 159 which is connected to base 122 by any suitable means such as sonic welding. For this purpose, sonic energy directors 159a are provided on plate 159 to aid in the sonic welding step (see FIGS. 14 and 16). Passageway 158 is, in turn, in communication with reservoir 130 via flow control means here provided as a rate control frit 160 which is housed within a cavity 162 formed in base 122 proximate the outlet 130a of reservoir 130. Frit 160 can be constructed from various materials including stainless steel, porous plastic or porous ceramics of the character available from Ball Brothers Company of Boulder, Colo. Frit 160 can also be constructed from a polyether ether Ketone (PEEK) material which is readily commercially available from Upchurch Scientific, Inc. of Seattle, Wash. and is more fully described in U.S. Pat. No. 5,651,931.

Figure 19:
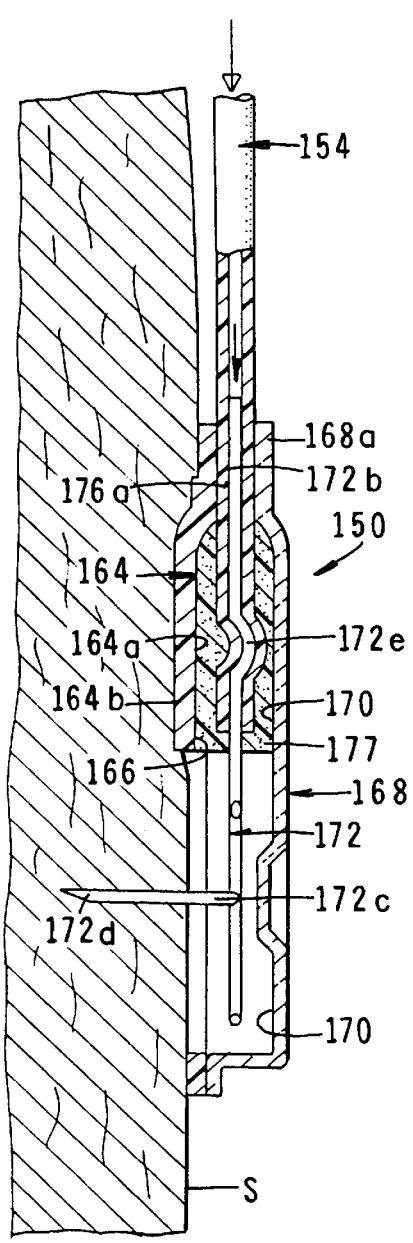
FIG. 19 is a cross-sectional view taken along lines 19—19 of FIG. 17 showing the infusion means connected to the patient.
Figure 20:
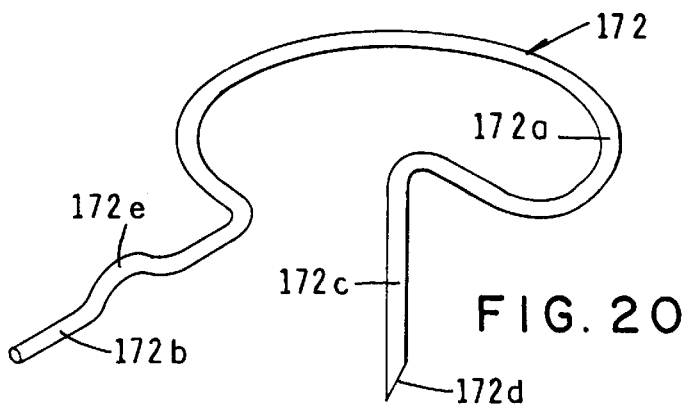
FIG. 20 is a generally perspective view of the infusion cannula of the apparatus shown in FIG. 17.

Turning particularly to FIGS. 19 and 20, the details of construction of the subcutaneous infusion device 150 is there shown. Device 150 here comprises a base 164 having upper and lower surfaces 164a and 164b and a generally circular shaped opening 166. Connected to base 164 is a cover 168. Cover 168 and base 164 cooperate to define an internal chamber 170 within which a generally spiral shaped cannula 172 is dynamically mounted. Cannula 172 includes a circuitously shaped body portion 172a which is disposed within chamber 170 and a stem portion 172b which is mounted between base 164 and cover 168 in a manner presently to be described. Cannula 172 also includes an outlet end, here provided in the form of a needle-like segment 172c, which extends generally perpendicularly downward from lower surface 164b of base 164 for subdermal infusion of medicinal fluids into the patient. For this purpose, segment 172c is provided with a sharp, pointed extremity 172d (see FIG. 20).

As shown in FIG. 19, stem portion 172b of the very small diameter spiral cannula 172 is encased within the inboard end 176a of fluid delivery tube 154 and the assembly thus formed is uniquely supported between a stem portion 168a of cover 168 (FIG. 17) and base 164 by a cannula encapsulation means shown here as a standard potting compound 177. Compound 177 rigidly supports the inboard end of tube 154 and portion 172b of the cannula so as to provide a secure interconnection of the cannula with base 164 and cover 168. As best seen in FIG. 20, portion 172b of the cannula is provided with a bend 172e to better secure the assemblage in place.

In using the device of this latest form of the invention, after the administration set has been suitably interconnected with the fluid delivery portion of the apparatus by means of delivery tube 154 in the manner shown in FIG. 17, infusion device 150 can be interconnected with the patient for subdermal delivery of fluids from the fluid delivery portion of the apparatus. This is accomplished by penetrating the patient's skin and tissue "S" with the point 172*d* of the infusion cannula in the manner shown in FIG. 19. In this regard, it is to be noted that an extremely important aspect of the infusion device 150 resides in the novel design of the circuitous cannula 172 and its unique interconnection with the base 164 and cover 168 of the infusion device. With the highly novel construction shown in the drawings, when the device is connected to the patient with the needle portion 172*c* of the cannula penetrating the patient's body, as, for example, the patient's abdomen, normal movement by the patient will permit the cannula to move within chamber 170 while the base remains completely stationary. Without this important feature, normal movements by the patient causing flexing of the muscle and tissue would cause irritation and discomfort to the patient. Additionally, such movements could cause the small diameter cannula to fail catastrophically or could cause separation of the device from the patient's skin. However, the novel and unique dynamic mounting of the cannula within chamber 170 positively prevents breaking of the fragile cannula and at the same time prevents irritation to the patient as a result of normal muscle flexing by the patient.

Figure 21:
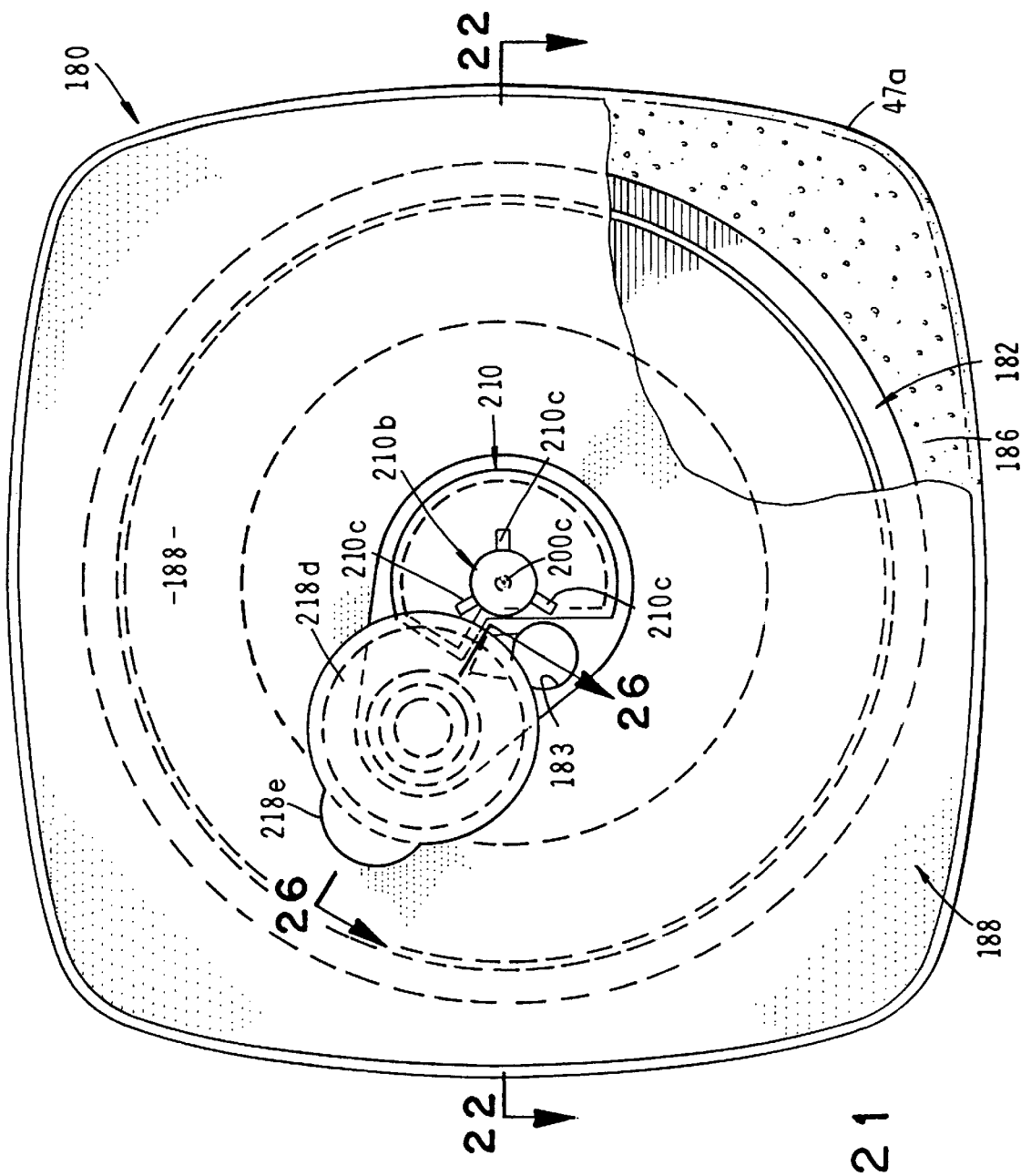
FIG. 21 is a bottom plan view of another embodiment of the fluid delivery device of the invention.
Figure 22:
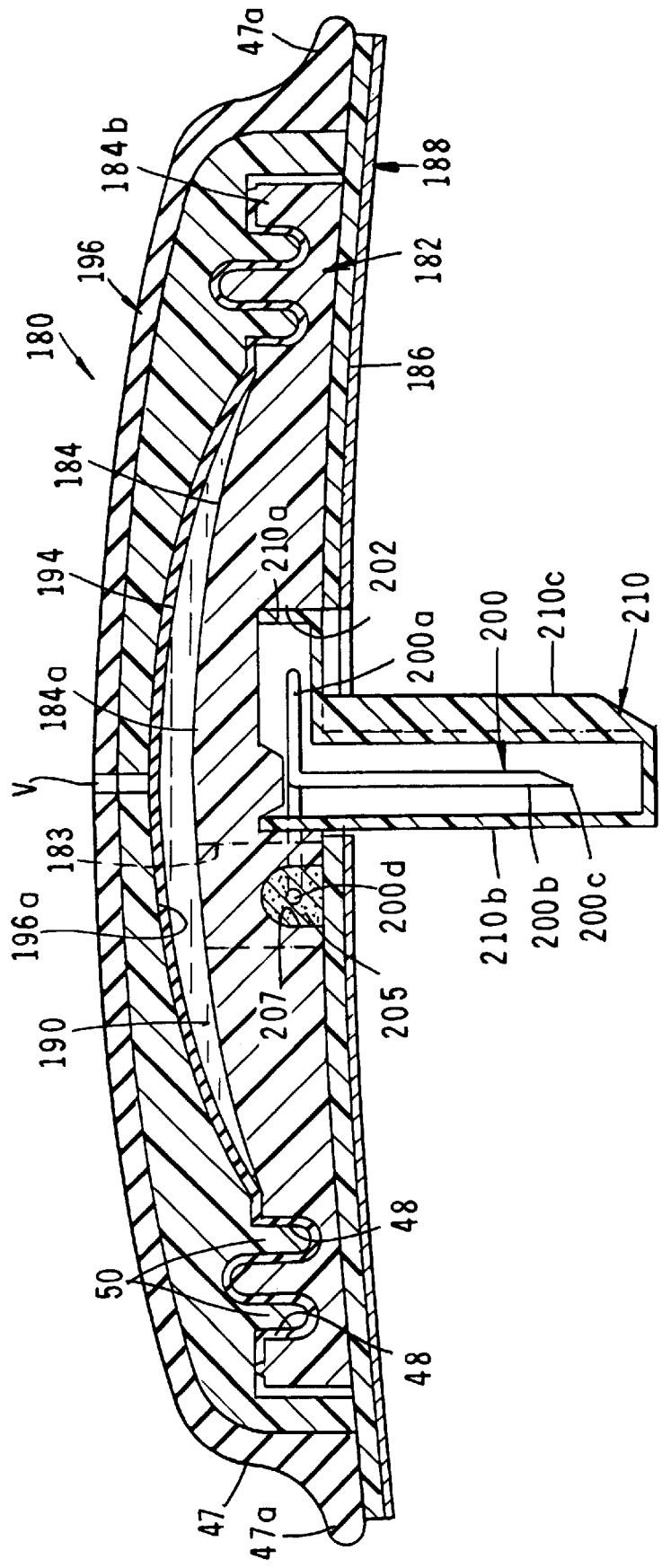
FIG. 22 is a cross-sectional view taken along lines 22—22 of FIG. 21.

Referring next to FIGS. 21 through 28, yet another embodiment of the invention is there shown and generally designated by the numeral 180. The apparatus of this latest form of the invention is similar in some respects to the embodiment shown in FIGS. 1 through 6 save that in this latest embodiment, the infusion cannula is dynamically mounted to the base. This latest form of the invention, which is also specially designed for subdermal infusion of selected medicaments, comprises a base 182 having an upper surface 184 including a generally dome shaped central portion 184*a* and a peripheral portion 184*b* circumscribing central portion 184*a*. As best seen in FIGS. 22 and 23, base 182 is also provided with a lower surface 186 to which a patient interconnection means or adhesive pad assembly 188 is connected. As before, pad assembly 188, which comprises a foam tape having adhesive on both sides, functions to releasably interconnect the device to the patient so as to hold it securely in place during the medicament delivery step.

Figure 26:
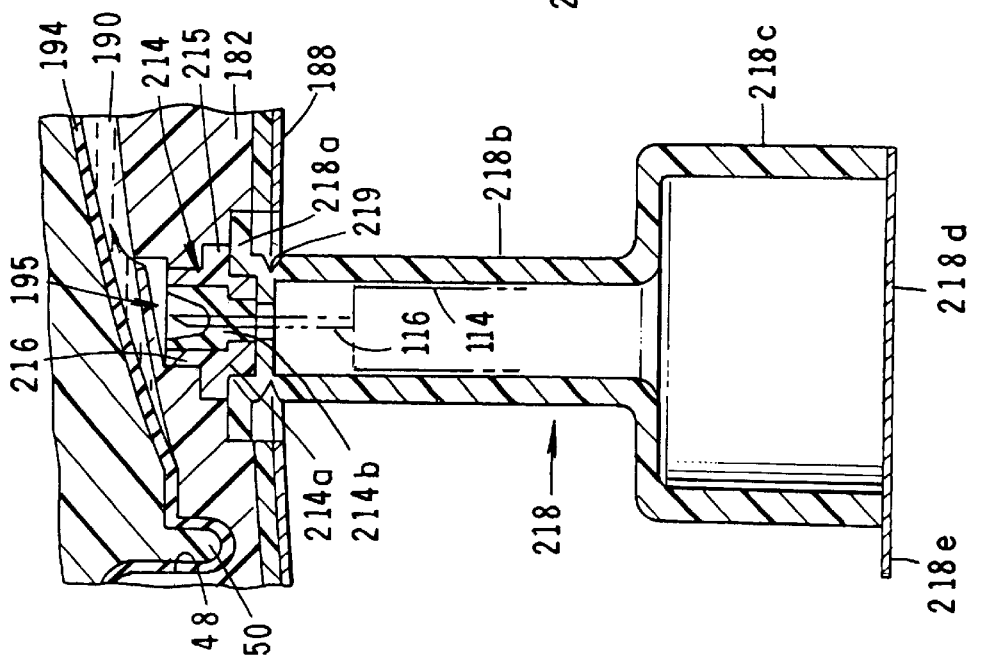
FIG. 26 is a cross-sectional view taken along lines 26—26 of FIG. 21.

A stored energy means cooperates with the upper surface 184*a* of base 182 to form a reservoir 190 (FIG. 22) having an inlet port assembly 195 (FIG. 26), which, in a manner presently to be described, is adapted to cooperate with a filling means for filling reservoir 190 with the medicinal fluid to be infused into the patient. The stored energy means is here provided in the form of at least one distendable membrane 194 which is superimposed over base 182. Membrane 194 is distendable as a result of pressure imparted on the membrane by fluids introduced into reservoir 190 via an inlet port assembly 195 (FIG. 26). As membrane 194 is distended in the manner shown in FIG. 22, internal stresses will be established, which stresses tend to move the membrane toward a less distended configuration and in a direction toward base 182.

Provided within the reservoir of the device, which is defined by the upper surface of the base and a concave surface 196*a* of a cover means for covering the distendable membrane, is ullage defining means for providing ullage within the reservoir and for engagement with membrane 194 as the membrane moves toward its less distended starting configuration. As before, the ullage defining means here comprises the dome shaped central portion 184*a* of base 182. When the distendable membrane, after being distended, tends to return toward its less distended configuration, fluid contained within the reservoir 190 will flow uniformly outwardly of the reservoir through the infusion means of the invention for infusing medicinal fluids into the patient.

Superimposed over base 182 is the cover means, shown here as a rigid cover 196 which functions, through the use of novel sealing means, to sealably enclose membrane 194. The sealing means is identical to that described in connection with the embodiment of FIGS. 1 through 6 and comprises a pair of generally circular grooves 48 formed in peripheral surface 184*b* of base 182 and a pair of cooperating, circular rim like protuberances 50 formed on the lower surface 196*b* of cover 196. As before, protuberances 50 are receivable within grooves 48 in the manner shown in FIG. 22 and function to sealably clamp distendable membrane 194 between the cover and the base.

Figure 24:
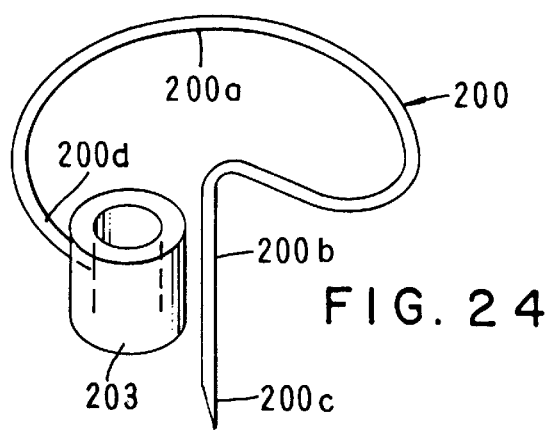
FIG. 24 is an enlarged, generally perspective view of the dynamically mounted cannula assembly of the embodiment of the invention shown in FIG. 23.
Figure 25:
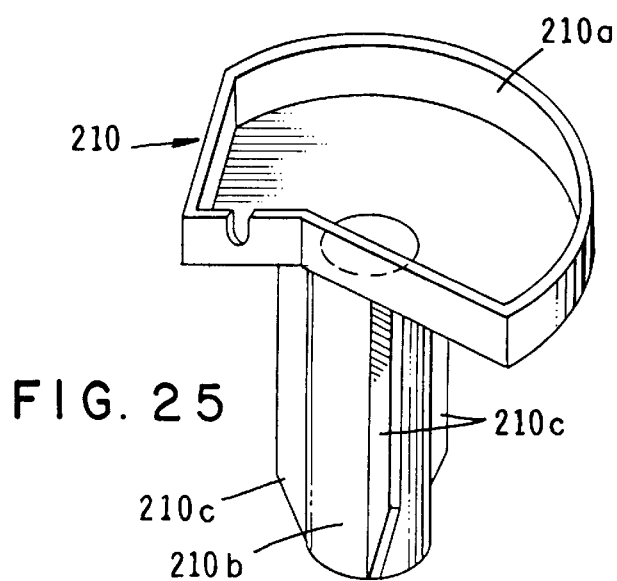
FIG. 25 is an enlarged, generally perspective view of the protective sheath of the embodiment shown in FIG. 23 which covers a portion of the dynamically mounted cannula assembly.

Referring particularly to FIGS. 22, 23, and 24, the infusion means of this latest form of the invention for subdermal infusion of medicaments into the patient can be seen to include a uniquely shaped, hollow cannula 200 which is dynamically mounted within an internal cavity 202 formed in base 182 (FIG. 23). As best seen in FIG. 24, cannula 200 includes a circuitously shaped body portion 200*a*, a portion of which is disposed within chamber 202. Cannula 200 also includes an outlet end, here provided in the form of a needle-like segment 200*b*, which extends generally perpendicularly downward from lower surface 186 of base 182 for subdermal infusion of medicinal fluids into the patient. For this purpose, segment 200*b* is provided with a sharp, pointed extremity 200*c* (see FIG. 22).

As shown in FIGS. 22, 23, and 24, inboard end portion 200*d* of the very small diameter spiral cannula 200, which forms the cannula inlet, is mounted within a generally cylindrically shaped housing 203 which houses the flow control means of the invention. This flow control means here comprises a porous frit 59 of the character previously described and a filter 204. Housing 203 is received within a bore 183 formed in base 182 (FIG. 23) so as to position the body portion 200*a* of the cannula within a cavity 207 provided in base 182 (FIG. 23). A potting compound 205 fills cavity 207 and functions to rigidly support the body portion of the cannula so as to provide a secure interconnection between the cannula and the base 182 and at the same time permits dynamic movement of the outboard end of the cannula within chamber 202.

Surrounding cannula 200 is a uniquely configured protective shroud 210 which has an upper portion 210*a* which closely receives portion 200*a* of the cannula and a lower portion 210*b* which surrounds portion 200*b* of the cannula. Upper portion 210*a* of shroud 210 forms an interference fit with the wall of chamber 202 so as to hold the shroud securely in place.

In this latest form of the invention, the filling means for filling reservoir 190 comprises a septum assembly 214 which is of similar construction to the previously described septum assembly. Septum assembly 214 is sealably disposed within a fill port 216 formed in the intermediate portion of base 182 (see FIG. 26). Septum assembly 214 includes a septum housing 214*a* which is receivable within fill port 216 and an elastomeric, pierceable core 214*b* which is sealably disposed within an opening formed in septum housing 214*a*.

As best seen in FIGS. 26 and 29, septum housing 214*a* includes a generally circular shaped connector base 215 which is receivable within fill port 216 so that housing 214a can be adhesively or sonically bonded to base 182. Referring to FIG. 26, it is to be noted that a fill adapter 218 is provided for use in filling reservoir 190. Fill adapter 218 includes an upper flange 218a which is also receivable within fill port 216 for engagement with connector base 215 of the septum housing for interconnecting the fill adapter with the septum housing and with the base 182 as by adhesive bonding. Fill adapter 218 also includes an upper portion 218b and an enlarged diameter portion 218c. Provided proximate the juncture of portions 218b and flange 218a is a serration 219 which permits portion 218b to be easily broken away from flange 218a.

Figure 27:
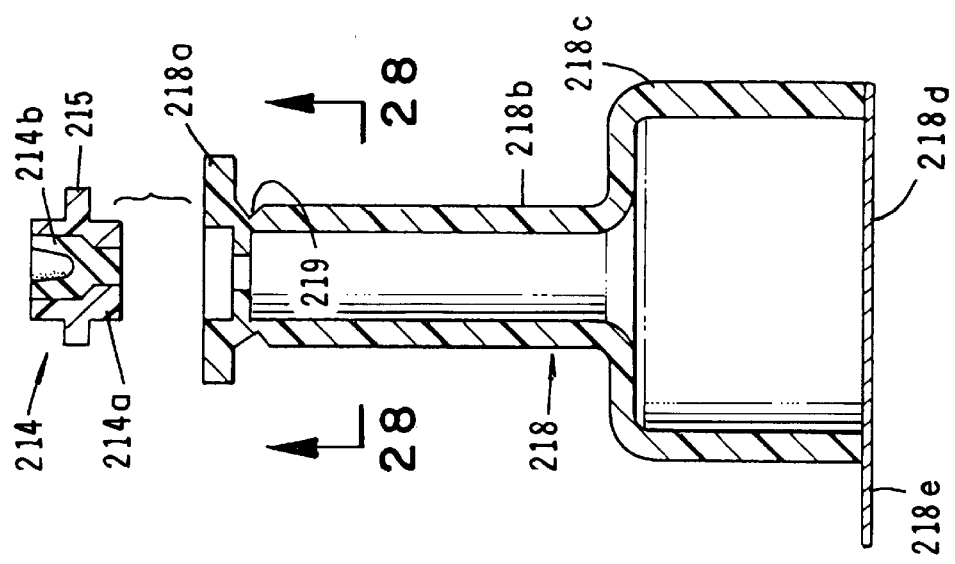
FIG. 27 is an exploded, cross-sectional view of the fill adapter assembly of the invention illustrated in FIG. 26.
Figure 28:
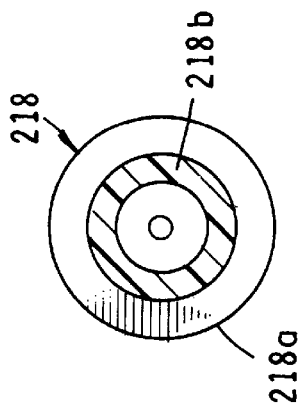
FIG. 28 is a cross-sectional view taken along lines 28—28 of FIG. 27.

Also forming a part of the filling means of the present invention is a filling syringe which is identical in construction and operation to filling syringe 106 shown in FIG. 11. In using the filling syringe 106 to fill reservoir 190 of the device of this latest form of the invention, protective cap 118 is first removed. Next, the tear away protective cover 218d which covers the open end of adapter 218 is removed by pulling on the pull tab 218e (FIGS. 21, 26, and 27). This done the needle housing 114 and needle 116 can be telescopically inserted into adapter 218. As the syringe assembly is urged inwardly of the adapter, needle 116 will pierce pierceable core 214b placing reservoir 190 of the device in fluid communication with reservoir 112a of medicament vial 112. Filling of reservoir 190 is accomplished in the manner previously described by urging vial adapter 92 forwardly over housing 120 so as to move plunger 89 forwardly of vial 112. (see FIG. 11).

In using the apparatus of this latest form of the invention, after reservoir 190 has been filled, portions 218b and 218c of the fill adapter are broken away from flange 218a along serrations 219 and cannula protective cap 210 is removed by gripping finger engaging ribs 210c so that the device can be interconnected with the patient. This is accomplished by penetrating the patient's skin and tissue "S" with the point 200c of the infusion cannula. When the device is thusly connected to the patient with the needle portion 200c of the cannula penetrating the patient's body, normal movement by the patient will once again permit the dynamically mounted cannula to move within chamber 202 while the base remains completely stationary thereby preventing irritation to the patient as a result of normal movement by the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery device for infusing medicinal fluids into a patient at a controlled rate comprising:
   (a) a base having a lower surface and a fill port;
   (b) stored energy means for forming, in conjunction with said base, a reservoir having an inlet port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) infusion means for infusing medicinal fluids from said fluid reservoir into the patient, said infusion means comprising a hollow cannula having an inlet in communication with said outlet port of said reservoir;
   (d) cover means connected to said base for covering said distendable membrane; and
   (e) filling means connected to said base for filling said reservoir, said filling means comprising:
      (i) a septum assembly, including a pierceable septum sealably disposed within said fill port of said base;
      (ii) a filling syringe having a housing, a fluid reservoir within said housing, and a hollow cannula carried by said housing for communication with said fluid reservoir; and
      (iii) a fill adapter connected to said lower surface of said base and extending outwardly therefrom, said fill adapter including a wall portion defining an opening closely receiving at least a portion of said housing of said filling syringe.

2. A device as defined in claim 1 in which said wall portion of said adapter defines a generally oval shaped opening and in which at least a portion of said housing of said filling syringe is generally oval shaped for insertion into said oval shaped opening.

3. A device as defined in claim 1 further including flow control means disposed between said reservoir and said infusion means for controlling fluid flow from said reservoir.

4. A device as defined in claim 1, further including ullage defining means disposed within said reservoir for providing ullage within said reservoir, said ullage defining means comprising a dome shaped protuberance formed on said base.

5. A device as defined in claim 1 in which said septum assembly comprises a septum housing receivable within said fill port of said base and an elastomeric, pierceable core sealably disposed within said septum housing.

6. A device as defined in claim 1 in which said hollow cannula of said infusion means is connected to and supported by said base.

7. A device as defined in claim 1 in which said hollow cannula of said infusion means is connected to a subcutaneous infusion device spaced a part from said base.

8. A device as defined in claim 1 in which said fill adapter is removably connected to said base.

9. A device as defined in claim 1 in which said fill adapter includes an upper wall portion and a lower wall portion, said lower wall portion being separable from said upper wall portion.

10. A fluid delivery device for infusing medicinal fluids into a patient at a controlled rate comprising:
   (a) a base having an upper surface including a central portion and a peripheral portion circumscribing said central portion, a lower surface engageable with the patient and an intermediate portion disposed between said upper and lower surfaces, said intermediate portion having a fill port formed therein;
   (b) stored energy means for forming, in conjunction with said base, a reservoir having an inlet port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) infusion means for infusing medicinal fluids from said fluid reservoir into the patient, said infusion means comprising a hollow cannula having an inlet in communication with said outlet port of said reservoir;

(d) cover means connected to said base for covering said distendable membrane; and (e) filling means connected to said base for filling said reservoir, said filling means comprising:
 (i) a septum assembly, including a pierceable septum sealably disposed within said fill port of said base;
 (ii) a filling syringe, including a housing, a container having a fluid reservoir disposed within said housing and a hollow piercing needle carried by said housing for communication with said fluid reservoir; and
 (iii) a fill adapter connected to said lower surface of said base, said fill adapter including an upper wall portion and a lower wall portion defining an opening closely receiving at least a portion of said housing of said filling syringe, at least a part of said fill adapter being removable from said base.

11. A device as defined in claim 10 in which said stored energy means comprises first and second distendable membranes.

12. A device as defined in claim 10 in which said wall portion of said adapter defines a generally oval shaped opening and in which at least a portion of said housing of said filling syringe is generally oval shaped for insertion into said oval shaped opening.

13. A device as defined in claim 10, further including ullage defining means disposed within said reservoir for providing ullage within said reservoir, said ullage defining means comprising a dome shaped protuberance formed on said base.

14. A device as defined in claim 10 in which said septum assembly comprises a septum housing receivable within said fill port of said base and an elastomeric, pierceable core sealably disposed within said septum housing.

15. A device as defined in claim 14 in which said septum housing includes a non-circular shaped connector base and in which said fill adapter includes a connector means for engagement with said non-circular shaped connector base for interconnecting said fill adapter with said septum housing upon rotation of said fill adapter relative to said septum housing.

16. A device as defined in claim 14 in which said lower wall portion is separable from said upper wall portion.

17. A fluid delivery device for infusing medicinal fluids into a patient at a controlled rate comprising:
 (a) a base having an upper surface including a central portion and a peripheral portion circumscribing said central portion, a lower surface engageable with the patient and an intermediate portion disposed between said upper and lower surfaces, said intermediate portion having a fill port formed therein;
 (b) stored energy means for forming, in conjunction with said base, a reservoir having an inlet port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
 (c) infusion means for infusing medicinal fluids from said fluid reservoir into the patient, said infusion means comprising a hollow cannula having an inlet in communication with said outlet port of said reservoir;
 (d) flow control means disposed between said reservoir and said infusion means for controlling liquid flow from said reservoir;

(e) cover means connected to said base for covering said distendable membrane; and (f) filling means connected to said base for filling said reservoir, said filling means comprising:
 (i) a septum assembly, including a septum housing receivable within said fill port of said base and an elastomeric, pierceable core sealably disposed within said septum housing;
 (ii) a filling syringe, including a housing, a container having a fluid reservoir disposed within said housing and a hollow piercing needle carried by said housing for communication with said fluid reservoir; and
 (iii) a fill adapter removably connected to said lower surface of said base, said fill adapter including an upper wall portion and a lower wall portion defining an opening closely receiving at least a portion of said housing of said filling syringe, at least a part of said fill adapter being removable from said base.

18. A device as defined in claim 17 in which said septum housing includes a non-circular shaped connector base and in which said fill adapter includes a connector means for engagement with said non-circular shaped connector base for interconnecting said fill adapter with said septum housing upon rotation of said fill adapter relative to said septum housing.

19. A device as defined in claim 17 in which said wall upper portion of said adapter defines a generally oval shaped opening and in which at least a portion of said housing of said filling syringe is generally oval shaped for insertion into said oval shaped opening.

20. A device as defined in claim 17, further including ullage defining means disposed within said reservoir for providing ullage within said reservoir, said ullage defining means comprising a dome shaped protuberance formed on said base.

21. A device as defined in claim 17 in which said stored energy means comprises first and second distendable membranes.

22. A device as defined in claim 17 further including means for sealably closing said opening in said lower wall portion of said fill adapter.

23. A device as defined in claim 17 in which said flow control means comprises a porous flow rate control frit.

24. A device as defined in claim 17 in which said flow control means comprises a flow control wafer having a very small laser drilled aperture formed therein.

25. A device as defined in claim 17 in which said cover means includes a soft, pliable elastomeric overcover.

26. A device as defined in claim 17 in which said cover means includes a soft, pliable elastomeric overcover having resiliently deformable edge and corner portions.

27. A device as defined in claim 17 in which one of said cover means and said base includes at least one generally circular groove and in which the other of said cover means and said base includes at least one protuberance receivable within said groove.

28. A device as defined in claim 17 in which said cover means comprises a cover having a pair of generally circular shaped, rim-like protuberances and in which said base includes a pair of generally circular shaped grooves indexable with said protuberances.

29. A device as defined in claim 28 in which a portion of said distendable membrane is disposed between said protuberances and said grooves.

* * * * *